US011160509B2

(12) United States Patent
Gupta et al.

(10) Patent No.: US 11,160,509 B2
(45) Date of Patent: Nov. 2, 2021

(54) METHODS AND SYSTEMS OF DE-NOISING MAGNETIC-FIELD BASED SENSOR DATA OF ELECTROPHYSIOLOGICAL SIGNALS

(71) Applicant: Analytics For Life Inc., Toronto (CA)

(72) Inventors: Sunny Gupta, East York (CA); Mohsen Najafi Yazdi, Toronto (CA)

(73) Assignee: Analytics for Life Inc., Toronto (CA)

( * ) Notice: Subject to any disclaimer, the term of this patent is extended or adjusted under 35 U.S.C. 154(b) by 462 days.

(21) Appl. No.: 16/165,641

(22) Filed: Oct. 19, 2018

(65) Prior Publication Data

US 2019/0117164 A1 Apr. 25, 2019

Related U.S. Application Data

(60) Provisional application No. 62/574,979, filed on Oct. 20, 2017.

(51) Int. Cl.
| | |
|---|---|
| *A61B 5/243* | (2021.01) |
| *A61B 5/00* | (2006.01) |
| *A61B 5/245* | (2021.01) |
| *A61B 5/372* | (2021.01) |
| *A61B 5/346* | (2021.01) |

(Continued)

(52) U.S. Cl.
CPC .......... *A61B 5/7203* (2013.01); *A61B 5/0205* (2013.01); *A61B 5/053* (2013.01); *A61B 5/243* (2021.01); *A61B 5/245* (2021.01); *A61B 5/327* (2021.01); *A61B 5/346* (2021.01); *A61B 5/372* (2021.01); *A61B 5/7225* (2013.01); *A61B 5/7239* (2013.01); *A61B 5/7242* (2013.01); *A61B 5/7267* (2013.01);

(Continued)

(58) Field of Classification Search
None
See application file for complete search history.

(56) References Cited

U.S. PATENT DOCUMENTS

| | | |
|---|---|---|
| 7,253,627 B1 | 8/2007 | Ahmed |
| 9,070,012 B1 | 6/2015 | Sieracki et al. |
| | (Continued) | |

OTHER PUBLICATIONS

Freund, Yoav, and Robert E. Schapire, "A decision-theoretic generalization of on-line learning and an application to boosting," European conference on computational learning theory. Springer, Berlin, Heidelberg, Journal of computer and system sciences 55, 119-139 (1997).

(Continued)

*Primary Examiner* — Ankit D Tejani
(74) *Attorney, Agent, or Firm* — Meunier Carlin & Curfman LLC

(57) ABSTRACT

The exemplified technology facilitates de-noising of magnetic field-sensed signal data (e.g., of an electrophysiological event) using signal reconstruction processes that fuse the magnetic field-sensed signal data with another sensed signal data (e.g., voltage gradient signal data) captured simultaneously with the magnetic field-sensed signal data. To this end, the purely algorithmic processing technique beneficially facilitates removal and/or filtering of noise from a sensor lead of a noisy captured source and rebuilds the signal for that lead from information simultaneously obtained from other leads of a different source. In some embodiments, a data are fused via a sparse approximation operation that uses candidate terms based on Van der Pol differential equations.

19 Claims, 10 Drawing Sheets
(7 of 10 Drawing Sheet(s) Filed in Color)

(51) Int. Cl.
  *A61B 5/327* (2021.01)
  *G16H 50/20* (2018.01)
  *A61B 5/0205* (2006.01)
  *A61B 5/053* (2021.01)
(52) U.S. Cl.
  CPC .......... *A61B 5/7282* (2013.01); *G16H 50/20* (2018.01); *A61B 2562/0223* (2013.01)

(56) References Cited

U.S. PATENT DOCUMENTS

| | | | |
|---|---|---|---|
| 9,192,319 | B2 | 11/2015 | Hou et al. |
| 9,289,150 | B1 | 3/2016 | Gupta et al. |
| 9,408,543 | B1 | 8/2016 | Gupta et al. |
| 9,597,021 | B1 | 3/2017 | Gupta et al. |
| 9,737,229 | B1 | 8/2017 | Gupta et al. |
| 2004/0075473 | A1 | 4/2004 | Llinas et al. |
| 2004/0260169 | A1 | 12/2004 | Sternnickel |
| 2009/0018429 | A1 | 1/2009 | Saliga et al. |
| 2010/0016752 | A1 | 1/2010 | Sieracki et al. |
| 2015/0133803 | A1 | 5/2015 | Gupta et al. |
| 2015/0212168 | A1 | 7/2015 | Shah et al. |
| 2015/0216426 | A1 | 8/2015 | Burton et al. |
| 2016/0183822 | A1 | 6/2016 | Gupta et al. |
| 2016/0223627 | A1 | 8/2016 | Shah et al. |
| 2016/0378936 | A1 | 12/2016 | Burton et al. |
| 2017/0119272 | A1 | 5/2017 | Gupta et al. |
| 2017/0281014 | A1 | 10/2017 | Luehmann et al. |

OTHER PUBLICATIONS

International Search Report and Written Opinion issued for Application No. PCT/IB2018/001337, dated Feb. 18, 2019, 13 pages.
Puce, et al., "A Review of Issues Related to Data Acquisition and Analysis in EEG/MEG Studies", Brain Sci. 2017, 7, 58; doi:10.3390/brainsci7060058.

METHODS AND SYSTEMS OF DE-NOISING MAGNETIC-FIELD BASED SENSOR DATA OF ELECTROPHYSIOLOGICAL SIGNALS

RELATED APPLICATION

This application claims priority to, and the benefit of, U.S. Provisional Application No. 62/574,979, filed Oct. 20, 2017, titled "Methods and Systems of De-Noising Magnetic-field Based Sensor Data of Electrophysiological Signals," which is incorporated by reference herein in its entirety.

BACKGROUND

Optically pumped magnetometers are passive magnetic field sensors that employ a laser and photodetector to detect changes in the resonance of a "sensing" gas in a vapor cell that are sensitive to minute changes in weak magnetic fields. These new types of sensors can provide ultra-sensitive detection of magnetic fields, for example, having field sensitivity in the 1 picotesla (pT)/√Hz noise range when operating in a low field or near zero field, environment. Because of such sensitivity, these sensors are also unfavorably influenced by ambient magnetic noise, including those of nearby instrumentation as well as the Earth's magnetic field, for example.

In medical applications, to image the magnetic field of, e.g., the heart or brain (as in magnetocardiography and magnetoencephalography, respectively), highly customized magnetic shielding techniques and devices/components are used to provide the low field, or near zero field, environment. Such shielding can be configured to contain the magnetic field or fields of interest within the shielded enclosure and to prevent external magnetic fields from entering the enclosure. In many applications, the cost of such shielding can be expensive, limiting the practical use of these optically pumped magnetometers, particularly for common medical imaging applications and procedures.

SUMMARY

The exemplified technology facilitates de-noising of magnetic, or paramagnetic, field-sensed signal data (e.g., from optically pumped magnetometers) of an electrophysiological event using signal reconstruction processes that fuse a magnetic field-sensed signal data set with another sensed signal data set (e.g., a voltage gradient signal data set) captured simultaneously with the magnetic, or paramagnetic, field-sensed signal data set. The purely algorithmic processing technique beneficially facilitates removal and/or filtering of noise from a sensor lead of a noisy captured source and rebuilds the signal for that lead from information simultaneously obtained from other leads of a different source. In some embodiments, the acquired magnetic, or paramagnetic, field-sensed signal data set and voltage gradient signal data set substantially overlap one another. In some embodiments, the sampling of the magnetic, or paramagnetic, field-sensed signal data set and the sampling of the voltage gradient signal data set are within a pre-defined skew; e.g., having a temporal skew among the channels of less than about 1 μs, and, in some embodiments, having a temporal skew among the channels of less than about 10 femtoseconds. When used to filter measurements of optically pumped magnetometer sensors, the exemplified technique can eliminate the need for a low field, or near zero field, operating environment and/or the accompanying requirement for shielding.

In an aspect, a method is disclosed to de-noise data associated with a first set of signals by generating a sparse approximation of a first signal data set (e.g., first biosignal data set) in conjunction with data associated with a second set of signals (e.g., second biosignal data set), wherein the approximated first signal data set is used in analysis to, e.g., non-invasively identify and/or measure or estimate a degree of myocardial ischemia, identify one or more stenoses, and/or localize and/or estimate fractional flow reserve. The method includes receiving, by one or more processors, i) a first signal data set associated with one or more first signals (e.g., magnetic-, or paramagnetic-, field-sensed signals) acquired from a first set of sensor leads associated with a first sensor type (e.g., magnetometer, optically pumped magnetometer) and ii) a second signal data set associated with a one or more second signals captured from a second set of sensor leads, associated with a second sensor type (e.g., biopotential surface probes), wherein the first sensor type is different from the second sensor type, and wherein the one or more first signals are simultaneously captured with the one or more second signals. The method further includes determining, by the one or more processors, one or more candidate basis functions searched through, and selected from, a dictionary of candidate basis functions, wherein the plurality of candidate functions is aggregable (e.g., as a linear combination of a weighted sum) to represent the sparse approximation of the first signal data set and the second signal data set; and determining, via the one or more processors, one or more physiological parameters of the subject (e.g., coronary physiological parameters of the subject selected from the group consisting of a fractional flow reserve estimation, a stenosis value, and a myocardial ischemia estimation) based in part on the of the sparse approximation of the first signal data set, or a data set derived therefrom (e.g., the low-energy subspace components of the sparse approximation of the first signal data set).

As used herein, the term "processor" refers to a physical hardware device that executes encoded instructions for performing functions on inputs and creating outputs. The processor may include one or more processors, each configured to execute instructions and process data to perform one or more functions associated with a computer for indexing images. The processor may be communicatively coupled to RAM, ROM, storage, database, I/O devices, and other interfaces. The processor may be configured to execute sequences of computer program instructions to perform various processes.

In some embodiments, the dictionary of candidate basis functions comprises a set of candidate basis functions derived from one or more homotopic non-linear differential equations, these homotopic non-linear differential equations having a homotopy class, wherein each candidate basis function of the set of candidate basis functions is a solution of a given homotopic non-linear differential equation having a specific first embedding parameter value from a set of first embedding parameter values (e.g., based on a nonlinearity parameter) capable of being searched (i.e., having a closed-form solution) and a specific second embedding parameter value from a set of second embedding parameter values (e.g., based on a frequency parameter) capable of being searched (i.e., having a closed-form solution). In some embodiments, the one or more homotopic non-linear differential equations are based on a Van der Pol-based differential equation.

In some embodiments, the sparse approximation operation of determining the plurality of candidate basis functions is performed according to cyclical coordinate descent using a set of Van der Pol candidates, wherein each set of the Van der Pol candidates is defined by a nonlinearity parameter value and a frequency parameter value. The cyclical coordinate descent operation, in some embodiments, searches for candidate terms by iteratively varying the values of the one or more nonlinearity parameters and the one or more frequency parameters.

In some embodiments, the one or more homotopic nonlinear differential equations is/are selected from the group consisting of Lorenz-based equations, Rössler-based equations, and a Van der Pol-based differential equation.

In some embodiments, the operation of determining the plurality of candidate basis functions is performed according to an algorithm or method selected from the group consisting of modified matching pursuit, evolvable mathematical models, symbolic regression, orthogonal matching pursuit, least absolute shrinkage and selection operator (LASSO), linear models optimized using cyclical coordinate descent, orthogonal search, fast orthogonal search, and any variations or combinations of any of the above.

In some embodiments, the sparse approximation of the first signal data set is a linear combination of weighted sums of a plurality of selected candidate basis functions, wherein low-energy subspace components of the sparse approximation of the first signal data set are a subset of these weighted sums.

In some embodiments, the low-energy subspace components comprise a last set percentile of the plurality of selected candidate basis functions, wherein the percentile is selected from the group consisting of about a last 10 percent, about a last 15 percent, about a last 20 percent, and about a last 25 percent.

In some embodiments, the sparse approximation of the first signal data set comprises a linear combination of over 100 selected candidate basis functions, wherein at least two candidate basis functions are selected at a plurality of successive stages (e.g., selected at each stage, or selected at each stage for a pre-defined number of terms) when determining the one or more candidate basis functions searched from the dictionary of candidate basis functions.

In some embodiments, the at least two selected candidate basis functions selected at each successive stage include i) a first candidate basis function derived from one or more homotopic non-linear differential equations having a homotopy class and ii) a second candidate basis function derived from one or more homotopic non-linear differential equations having a homotopy class. In some embodiments, the first candidate basis function is about 90 degree phase offset from the second candidate basis function.

In some embodiments, at least four candidate basis functions are selected at one or more successive stages when searched across the dictionary of candidate basis functions. The method further comprises determining, by the one or more processors, a plurality of values associated with a measure of the reduction of error (e.g., mean square error, weighted mean square error, maximum square error) of approximating the first signal data set, wherein a first set of at least two candidate basis functions are selected based for the highest values of the plurality of values associated with the measure of the reduction of error, and wherein a second set of two candidate basis functions are selected based for a next highest of the plurality of values associated with the measure of the reduction of error determined at a same successive stage.

In some embodiments, the first set of at least two candidate basis functions includes i) a first candidate basis function (e.g., a cosine homotopy class) derived from one or more homotopic non-linear differential equation having homotopic class and ii) a second candidate basis function (e.g., a sine homotopy class) derived from one or more homotopic non-linear differential equation having homotopic class, wherein the first candidate basis function has an about 90-degree phase offset from the second candidate basis function.

In some embodiments, the at least one of the candidate basis functions comprises a Van der Pol-based differential equation with a forcing function (e.g., a non-linear aperiodic forcing function).

In some embodiments, the Van der Pol-based differential equations with the forcing function is expressed as:

$$\ddot{x} - 2\mu\omega_i(1-x^2)\dot{x} + \omega_i^2 x = 0$$

wherein $\mu$ is an embedding parameter corresponding to a measure of nonlinearity (e.g., wherein the Van der Pol-based differential equation with the forcing function is numerically solved, e.g., via a method such as Runge-Kutta).

In some embodiments, the first signal data set comprises magnetic-, or paramagnetic-, field-sensed signal data.

In some embodiments, the first signal data set is captured from a surface-based vector magnetometer (e.g., a zero-field optically pumped magnetometer) configured to operate at room temperature (e.g., not at superconducting temperature, e.g., between about −30° C. to about +60° C.).

In some embodiments, the first signal data set is captured from a surface-based vector magnetometer configured to operate within an ambient magnetic field below 30 nanotesla (nT).

In some embodiments, the second signal data set comprises voltage gradient signal data.

In some embodiments, the second signal data set comprises signal data captured from sensors selected from the group consisting of i) a 12-lead surface potential sensing electrode system, ii) a 6-lead differential surface potential sensing electrode system, and iii) a 3-lead orthogonal surface potential sensing electrode system.

In some embodiments, the second signal data set comprises wide-band cardiac phase gradient signal data (e.g., having at a sampling frequency above about 10 KHz, e.g., above about 40 Khz, above about 80 KHz, above about 500 Khz) derived from biopotential signals simultaneously captured (e.g., having a skew less than about 100 μs) from a plurality of surface electrodes placed on surfaces of a mammalian body in proximity to a heart.

In some embodiments, the second signal data set comprises wide-band cerebral phase gradient signal data (e.g., having at a sampling frequency above about 10 KHz, e.g., above about 40 Khz, above about 80 KHz, above about 500 Khz) derived from biopotential signals simultaneously captured (e.g., having a skew less than about 100 μs) from a plurality of surface electrodes placed on surfaces of a mammalian head.

In some embodiments, the first signal data set is acquired from a different sensor type from that of the second signal data, wherein the first signal data is captured by a sensor system selected from the group consisting of a magnetic-resonance imaging (MRI) system, a computed tomography (CT) system, a positron emission tomography (PET) system, an ultrasound system, and an electrical impedance system.

In some embodiments, the first signal data set is acquired from a different sensor type from that of the second signal data set, wherein the second signal data is captured by a sensor system selected from the group consisting of a magnetic-resonance imaging (MRI) system, a computed tomography (CT) system, a positron emission tomography (PET) system, an ultrasound system, and an electrical impedance system.

In another aspect, a method is disclosed of generating a sparse approximation of the physiological data (e.g., electrophysiological or magneto-physiological) for use in analysis to non-invasively identify and/or measure or estimate a degree of myocardial ischemia, identify one or more stenoses, and/or localize and/or estimate fractional flow reserve. The method includes receiving, by one or more processors, a signal data set, wherein the signal data set is obtained from an acquired measurement of one more signals of the subject and wherein the signal data set has been obtained from measurements acquired via noninvasive equipment configured to measure properties of the subject's heart (e.g., the magnetic field produced by electric activity in the heart; voltage, impedance, or current fluctuations resulting from action potentials within the heart, or phase gradient information thereof). The method further includes determining, by the one or more processors, one or more candidate basis functions searched through, and selected from, a dictionary of candidate basis functions, wherein the plurality of candidate functions is aggregable (e.g., as a linear combination of weighted sum) to represent the sparse approximation of the signal data set, wherein the dictionary of candidate basis functions comprises a set of candidate basis functions derived from one or more homotopic non-linear differential equations having a homotopy class, wherein each of the candidate basis function of the set is a solution of a given homotopic non-linear differential equation having a specific first parameter value from a set of first parameter values (e.g., based on a nonlinearity parameter) that is capable of being searched (i.e., having a closed form solution) and a specific second parameter value from a set of second parameter values (e.g., based on a frequency parameter) that is capable of being searched (i.e., having a closed form solution); and determining, via the one or more processors, one or more physiological parameters of the subject (e.g., coronary physiological parameters of the subject selected from the group consisting of a fractional flow reserve estimation, a stenosis value, and a myocardial ischemia estimation) based in part on the sparse approximation of the signal data set, or a data set derived therefrom (e.g., low-energy subspace components of the sparse approximation of the signal data set).

In some embodiments, the one or more homotopic non-linear differential equations are based on a Van der Pol-based equation.

In some embodiments, the one or more homotopic non-linear differential equations are selected from the group consisting of Lorenz-based equations, Rössler-based equations, and a Van der Pol-based equation.

In some embodiments, the operation of determining the plurality of candidate basis functions is performed according to an algorithm or method selected from the group consisting of modified matching pursuit, evolvable mathematical models, symbolic regression, orthogonal matching pursuit, least absolute shrinkage and selection operator (LASSO), linear models optimized using cyclical coordinate descent, orthogonal search, fast orthogonal search, and any variations or combinations of any of the above.

In some embodiments, the sparse approximation of the first signal data set is a linear combination of weighted sums of a plurality of selected candidate basis function, wherein low-energy subspace components of the sparse approximation of the first signal data set is a subset of said weighted sums.

In another aspect, a system is disclosed of generating a sparse approximation of the first signal data set for use in analysis to non-invasively identify and/or measure or estimate a degree of myocardial ischemia, identify one or more stenoses, and/or localize and/or estimate fractional flow reserve. The system includes one or more processors; and a memory having instructions stored thereon, wherein execution of the instruction by the one or more processors, cause the one or more processors to perform any of the method steps described above.

In another aspect, a non-transitory computer-readable medium is also disclosed, having instructions stored thereon such that execution of the instructions by a processor causes the processor to perform the method described above. A system is also disclosed, having processors and instructions stored in memory such that execution of the instructions by the processor causes the processor to perform the method described above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Color drawings have been submitted in this application. The color drawings are necessary as the only practical medium by which aspects of the claimed subject matter may be accurately conveyed. For example, the claimed invention relates to the modeling of signals, and the color drawings of experimental results showing the modeling of the signals with various levels of visibility is necessary to illustrate features of the claims.

Figure 1:
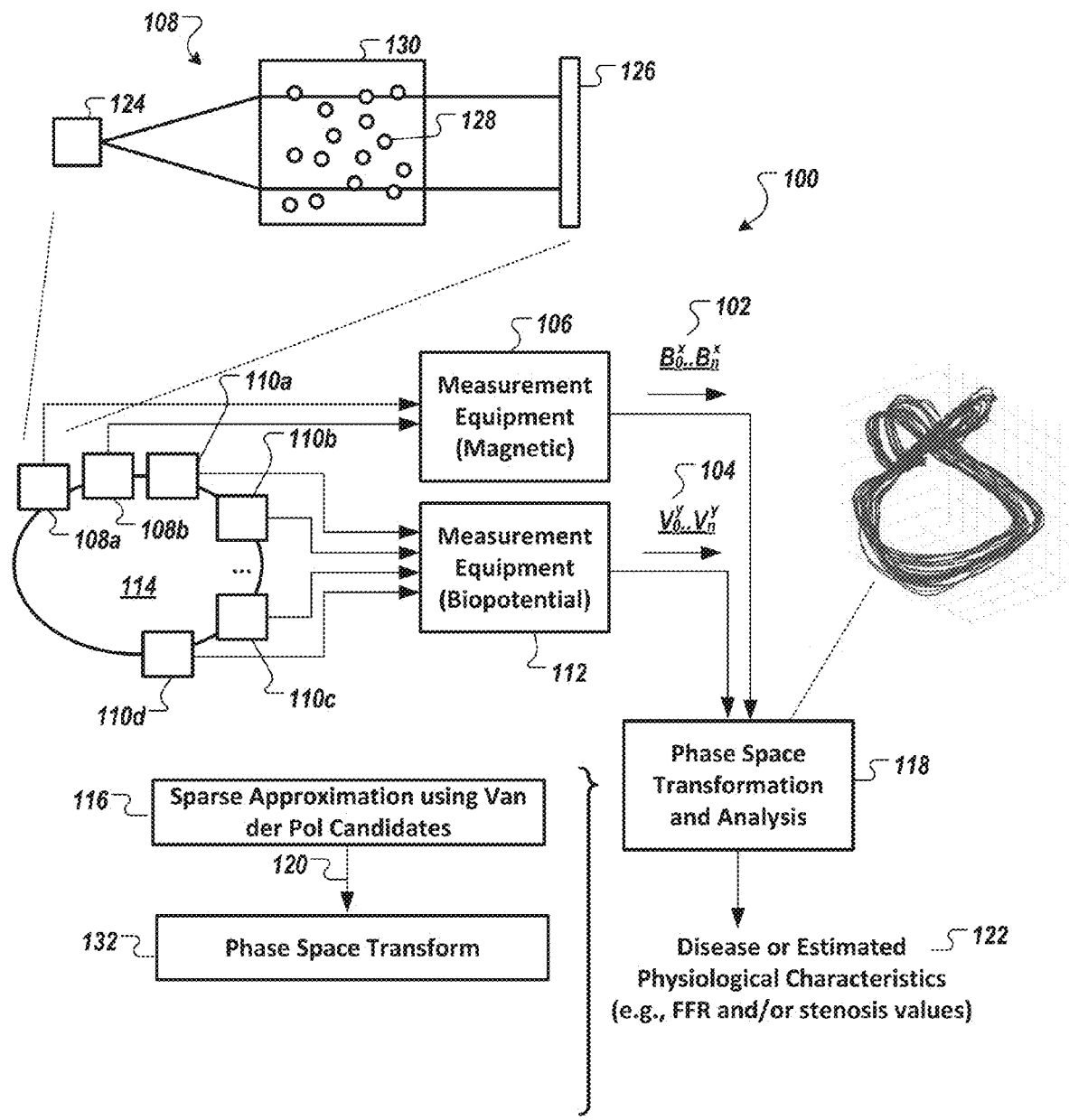

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 1 is a diagram of an example system according to the present disclosure that can de-noise a first signal data set by generating a sparse approximation of data in the first signal data set in conjunction with data in a second signal data set, in accordance with an illustrative embodiment.

Figure 2:
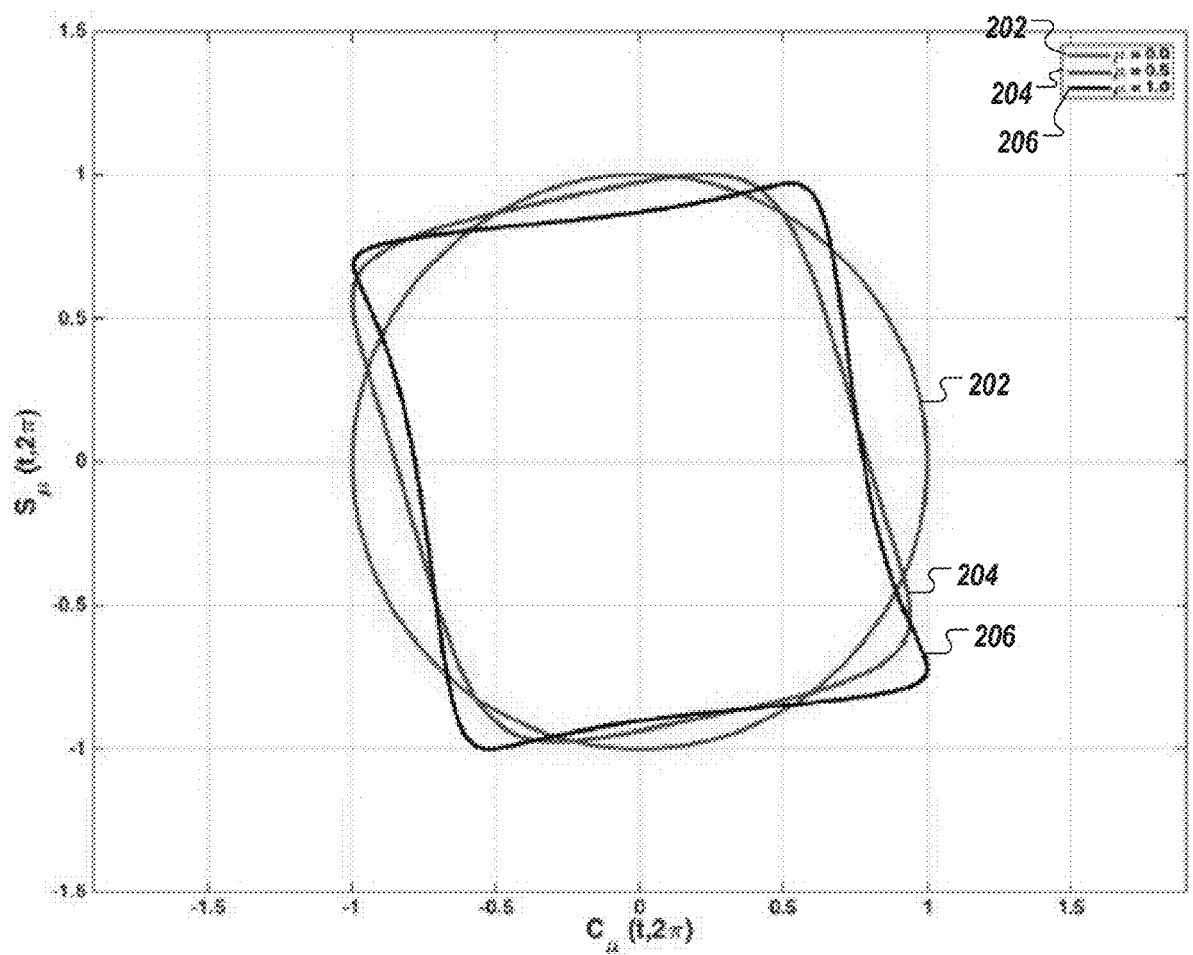

FIG. 2 shows a diagram of a phase space representation of Van der Pol candidates as a Sine Homotopy Class $S_\mu(t, \omega_i)$ and as a Cosine Homotopy Class $C_\mu(t, \omega_i)$ for three different parameter values used to generate the candidates.

Figure 3:
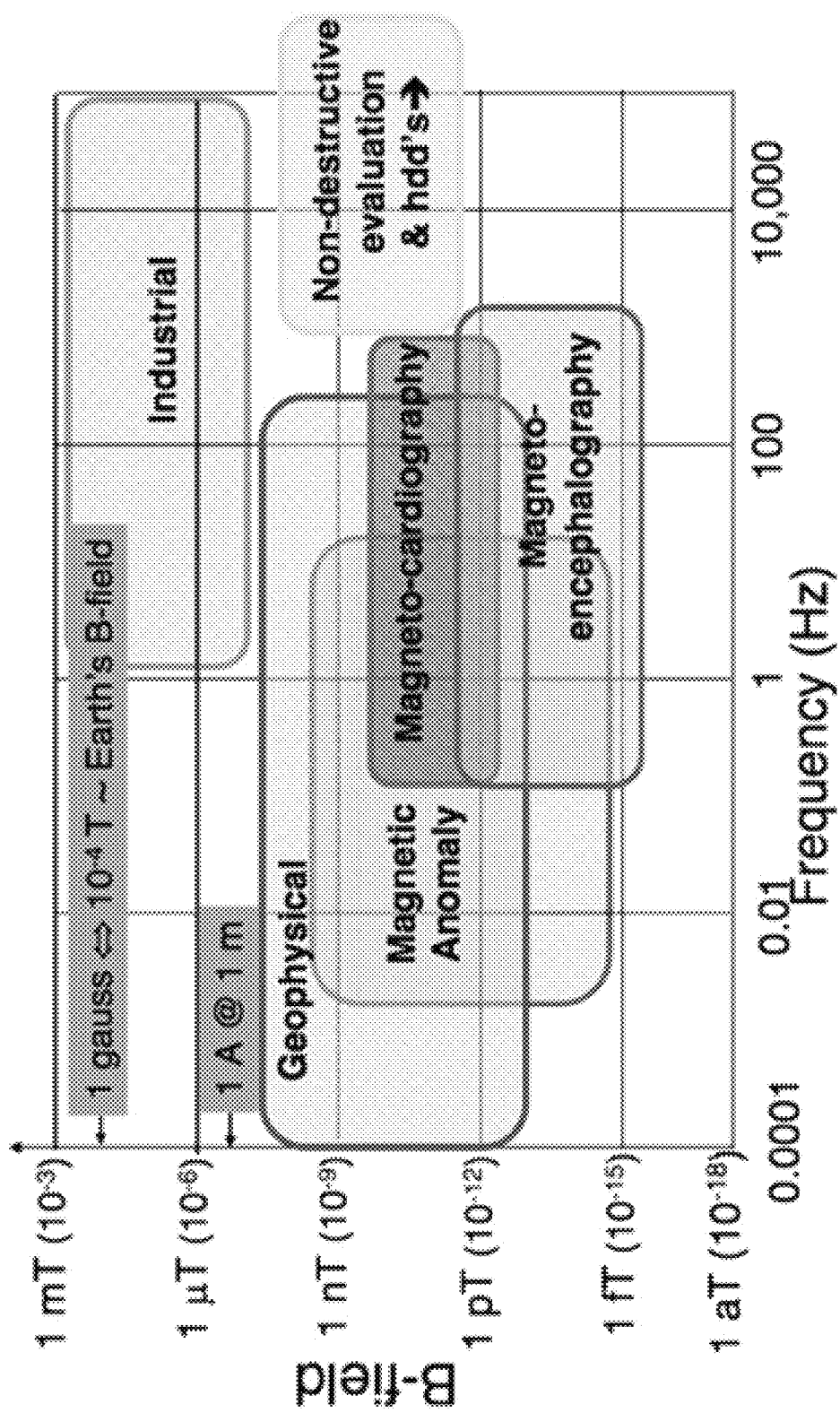

FIG. 3 shows a diagram of magnetic-field ranges typically used for magneto-cardiography and magneto-encephalography.

Figure 4:
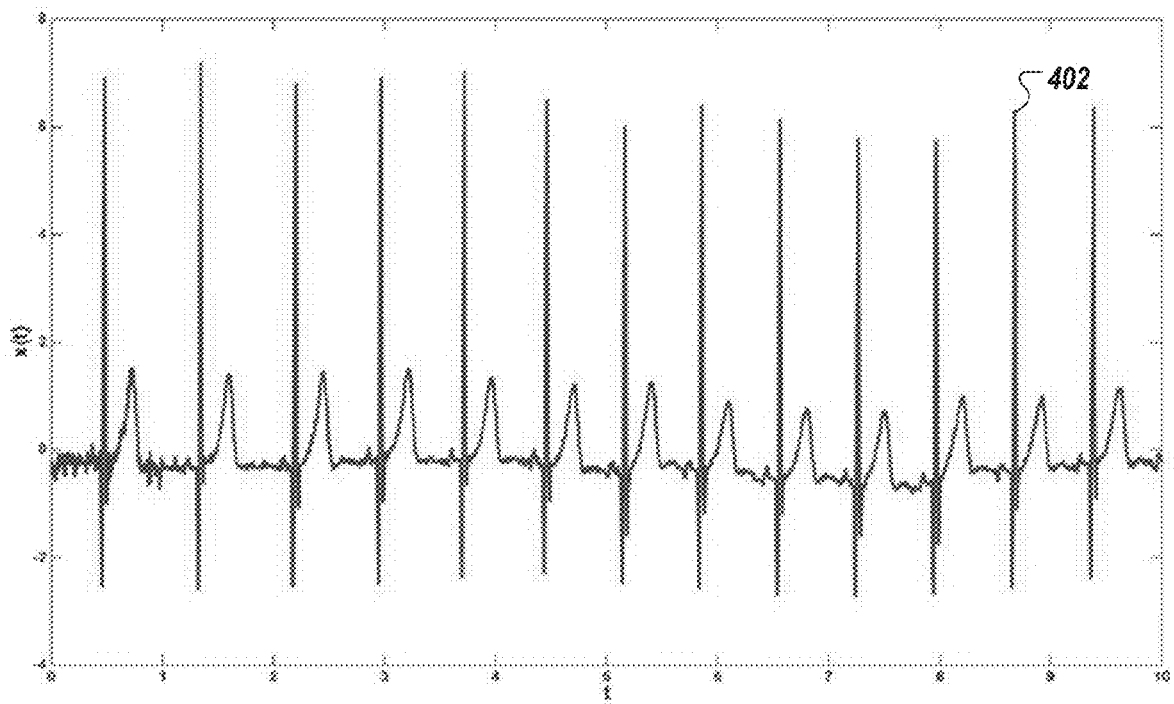
Figure 5:
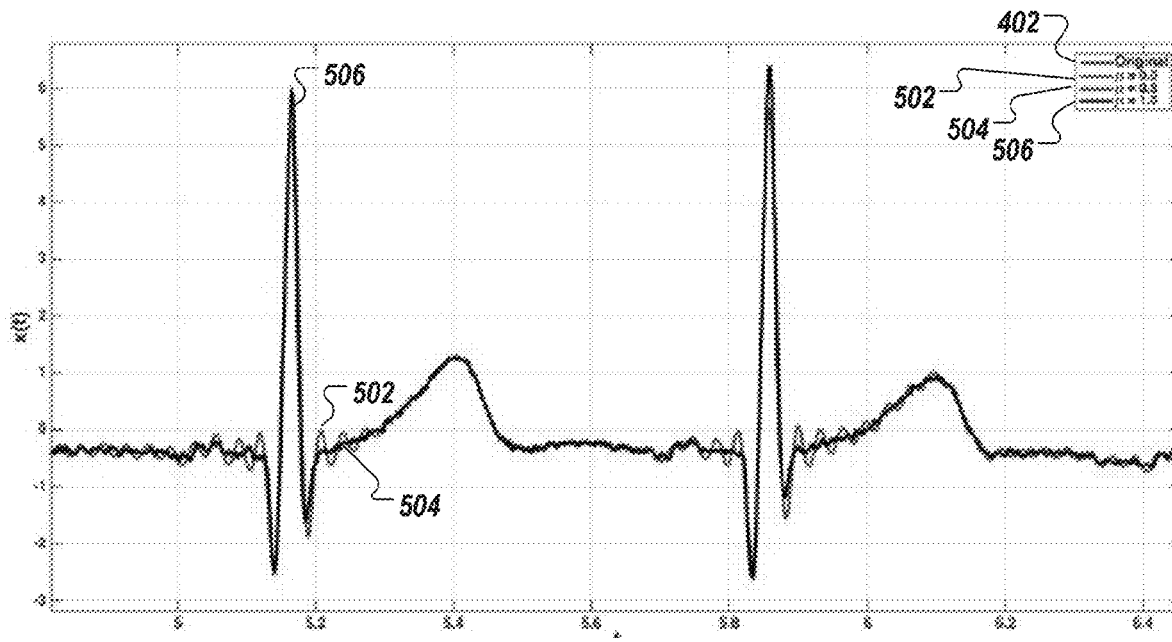

FIGS. 4 and 5 show example decomposition for a single lead cardiac biosignal using Van der Pol candidates, in accordance with an illustrative embodiment.

Figure 6:
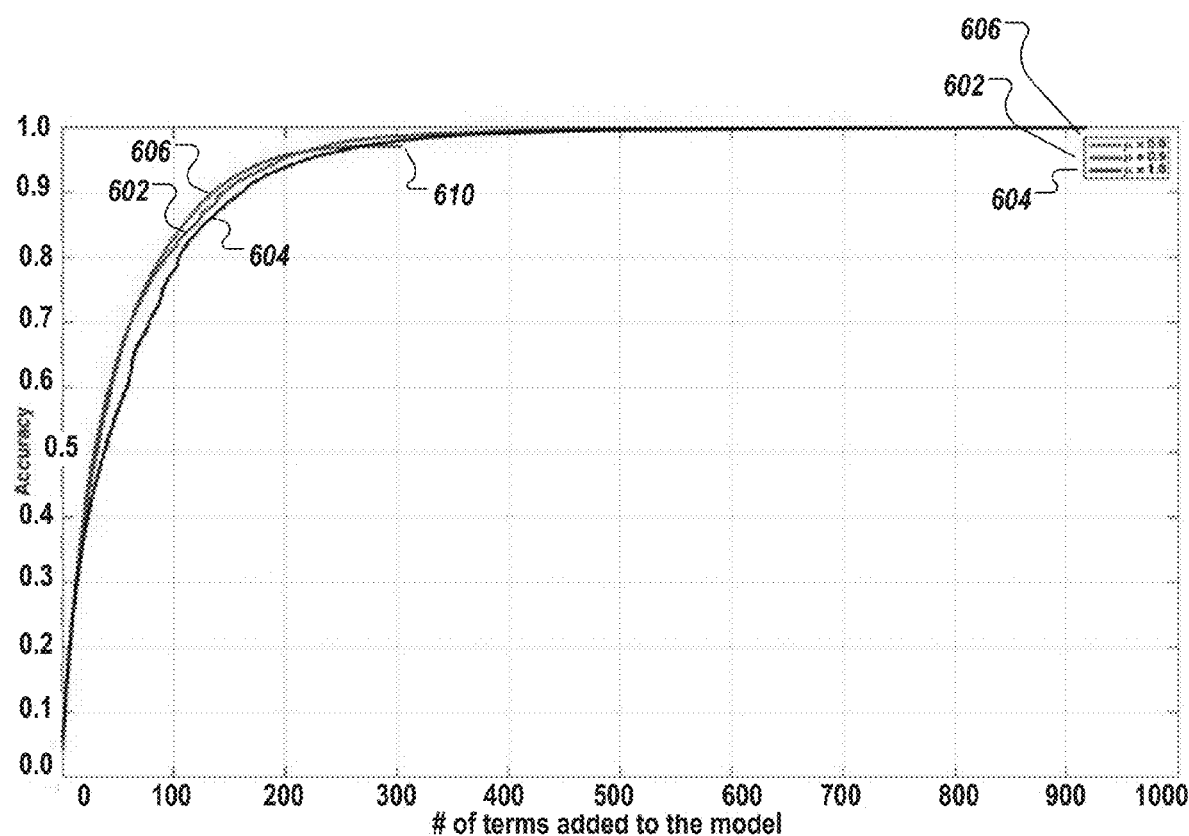

FIG. 6 shows a plot of model accuracies of Van der Pol candidate pools as a function of the number of terms used to represent the signal, in accordance with an illustrative embodiment.

Figure 7:
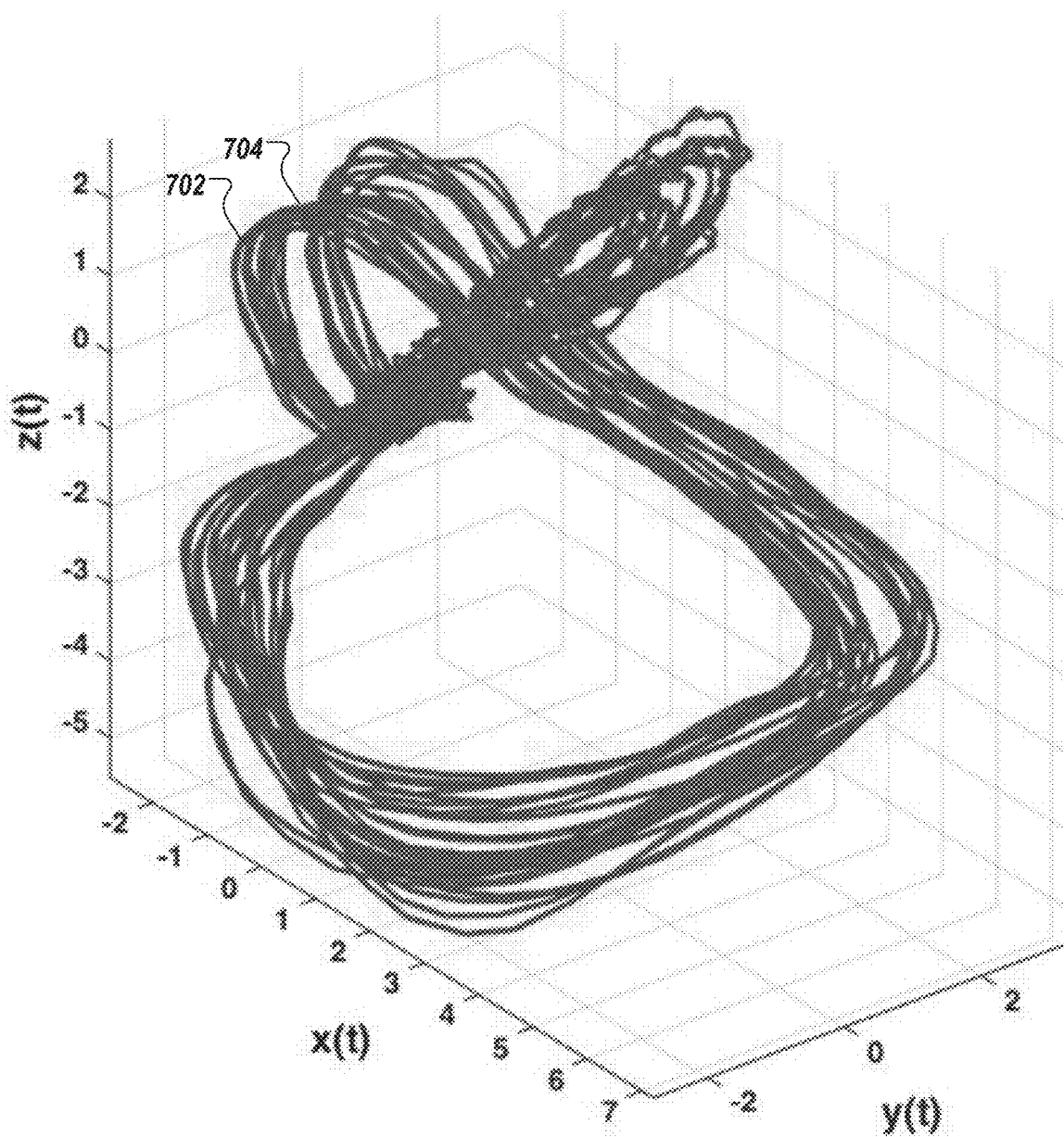

FIG. 7 shows a phase-space plot of an example decomposition for a three-lead cardiac biosignal, in accordance with an illustrative embodiment.

Figure 8:
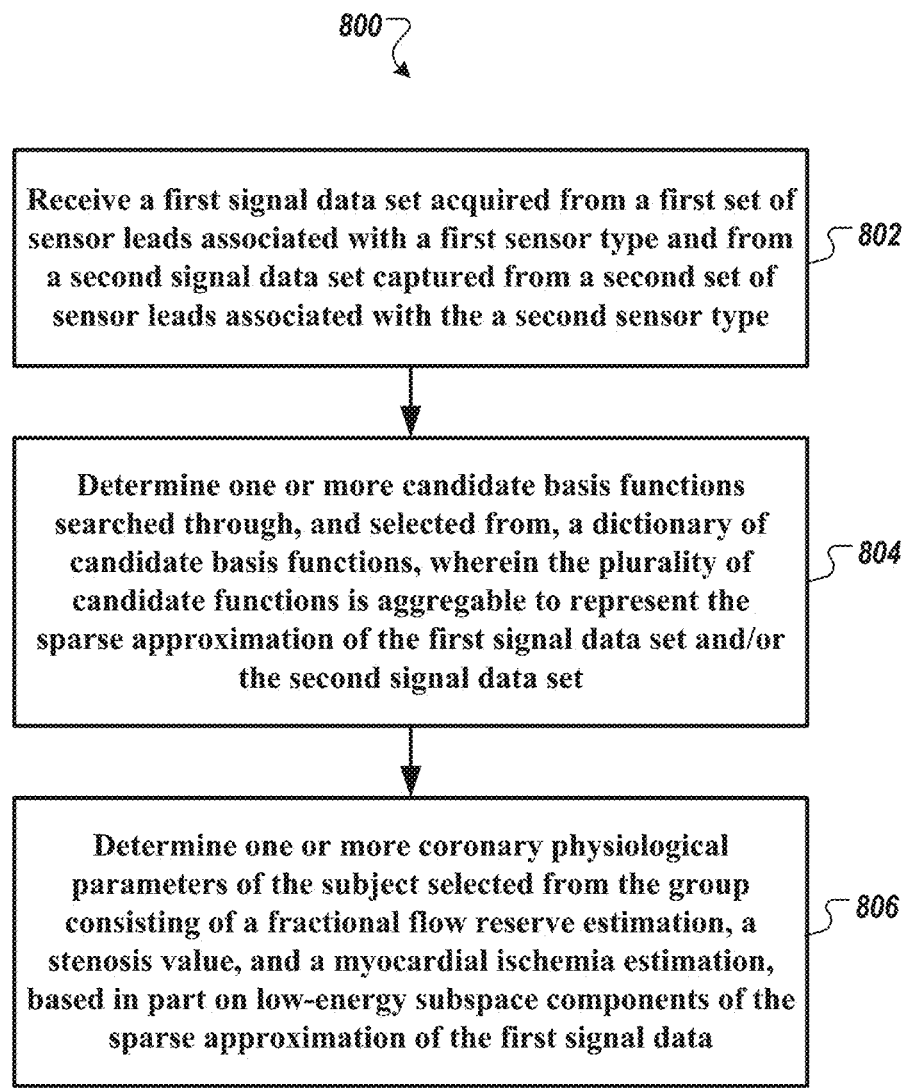

FIG. 8 is a diagram of a process to de-noise a first signal data set by generating a sparse approximation of the data therein in conjunction with data present in a second signal data set, in accordance with an illustrative embodiment.

Figure 9:
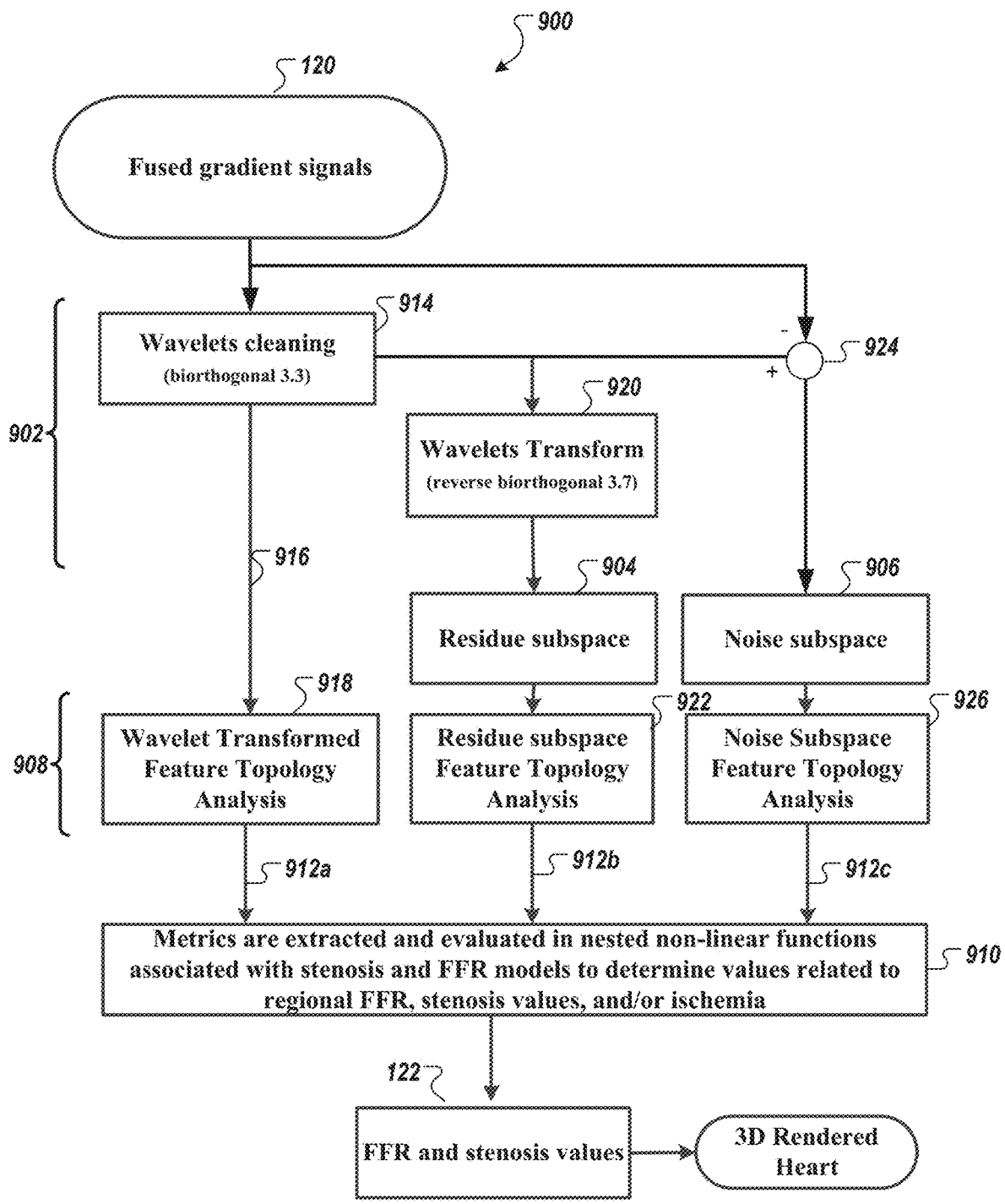

FIG. 9 is a diagram of an example method of processing the fused signal data set, in accordance with an illustrative embodiment.

Figure 10:
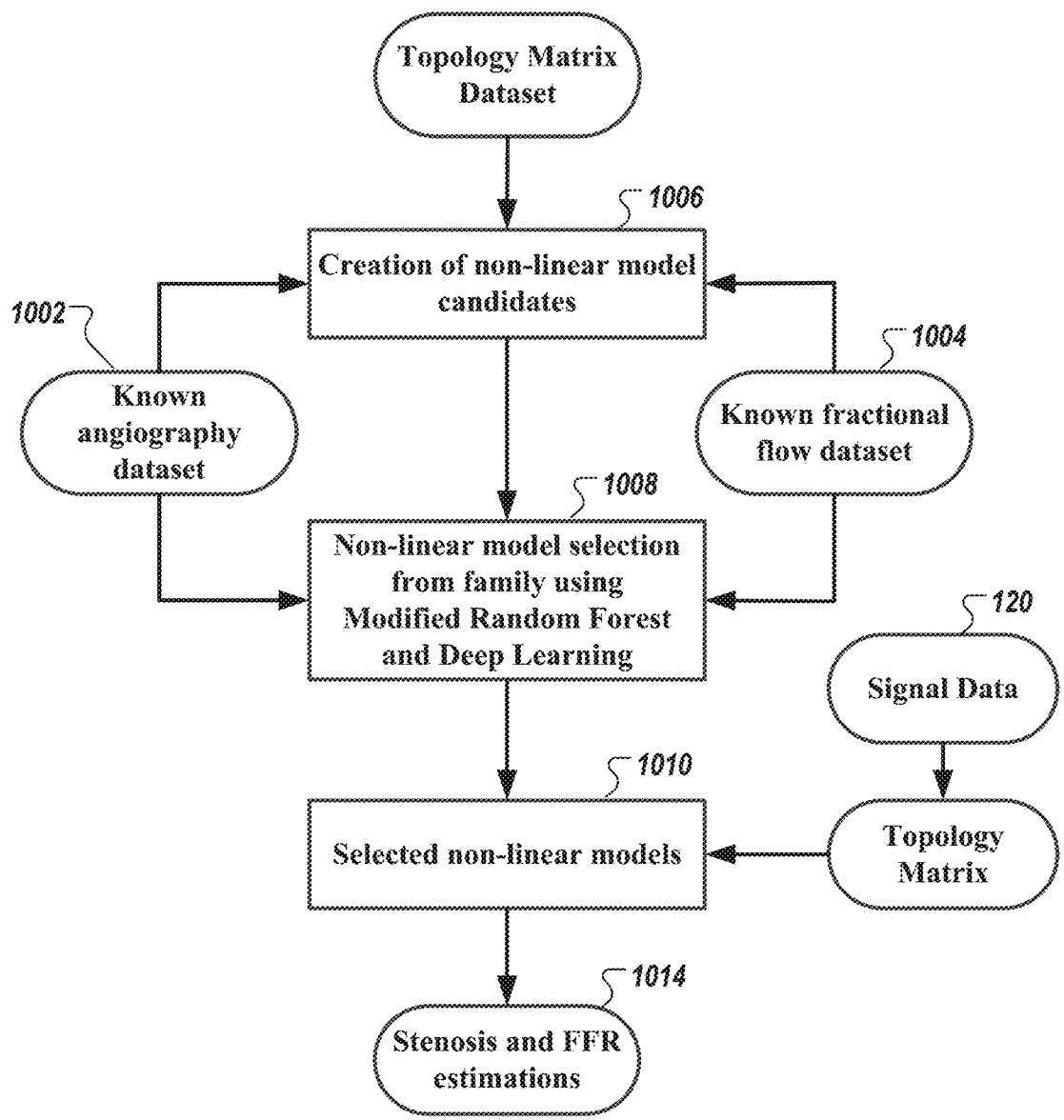

FIG. 10 is a diagram of a method of performing machine learning analysis to create and select non-linear models to identify and/or estimate a degree of myocardial ischemia, identify one or more stenoses, and/or localize and/or estimate fractional flow reserve, in accordance with an illustrative embodiment.

Figure 11:
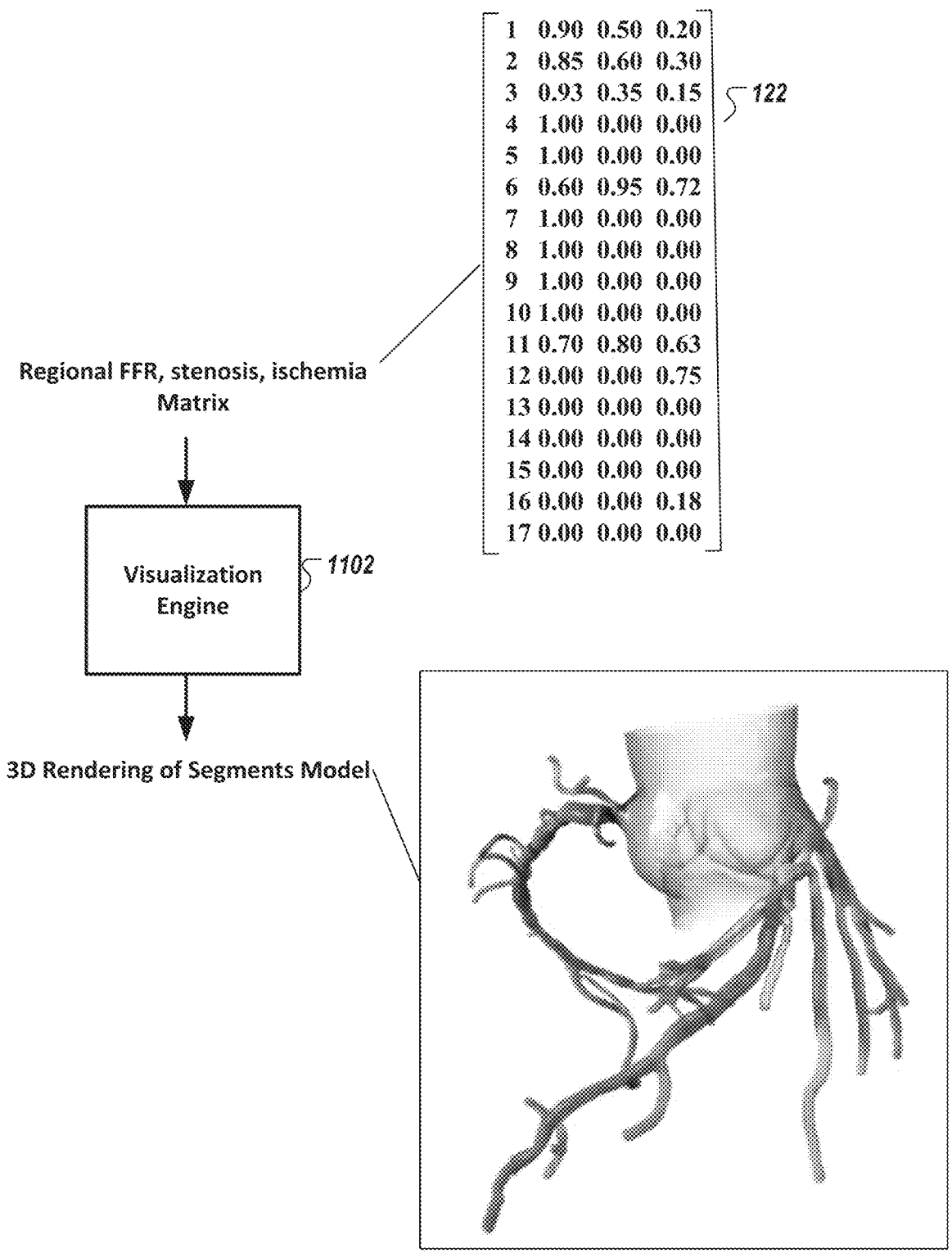

FIG. 11 is a diagram of a method of visualizing the estimated arterial flow characteristics in the heart, in accordance with an illustrative embodiment.

DETAILED SPECIFICATION

Each and every feature described herein, and each and every combination of two or more of such features is included within the scope of the present invention provided that the features included in such a combination are not mutually inconsistent.

Example System

FIG. 1 is a diagram of an example system 100 according to the present disclosure that can de-noise a first signal data set 102 by generating a sparse approximation of data in the first signal data set 102 in conjunction with data present in a second signal data set 104, in accordance with an illustrative embodiment. In FIG. 1, the first signal data set 102 is shown, including one or more time-series data ($B_0^x$ ... $B_n^x$) associated with one or more magnetic measurements of a specimen 114 (e.g., patient) acquired by magnetic- or paramagnetic-based measurement equipment 106 in which x is the number of associated magnetic, or paramagnetic, sensors 108 (shown as 108a and 108b) (e.g., one or more optically pumped magnetometers), and the second signal data set 104 is shown as one or more time-series data ($V_0^y$ ... $V_n^y$) associated with a biopotential measurement acquired by biopotential-based measurement equipment 112 in which y is the number of associated biopotential sensors 110 (shown as 110a, 110b, 110c, and 110d). Data in each of the first signal data set 102 and the second signal data set 104 are fused, or commonly represented by a set of common basis functions, via a sparse approximation operation 116 (shown as part of a "phase space transformation and analysis" operation 118) to generate a filtered or cleaned input data set 120 (of the first signal data set 102 and/or second signal data set 104). The generated filtered or cleaned input data set 120 (also referred to herein as a fused signal data set 120) can then be used in a subsequent part of the analysis 118 to non-invasively identify and/or measure and/or estimate a degree of morbidity (for, e.g., disease states and/or conditions such as myocardial ischemia, presence of a stenosis, etc.) or physiological characteristics (e.g., fractional flow reserve, etc.) (122). As shown in FIG. 1, the sparse approximation operation 116 is performed prior to the first signal data set 102 and/or the second signal data set 104 being converted via, a phase space transformation operation 132 to phase space coordinates.

Sparse approximation operation (e.g., 116) comprises a set of operations, often iterative, to find a best matching projection of a data set (e.g., multi-dimensional data) onto candidate functions in a dictionary. Each dictionary can be a family of waveforms that are used to decompose the input data set. The candidate functions, in some embodiments, are linearly combined to form a sparse representation of the input data set. These operations can be numerical or analytical. Examples of sparse approximation operation techniques/algorithms or methods include modified matching pursuit, evolvable mathematical models, symbolic regression, orthogonal matching pursuit, LASSO, linear models optimized using cyclical coordinate descent, orthogonal search, fast orthogonal search, and cyclical coordinate descent. The recited examples are not exhaustive, and other sparse approximation algorithms or methods may be used as well as any variations and combinations thereof.

De-noised magnetic, or paramagnetic, field-sensed signal data set (e.g., captured without a shielding system) generated from a fusion with voltage gradient signal data using the exemplified processes can have similar signal-to-noise characteristics to those of signals captured by a same sensor but in a significantly shielded environment. In some embodiments, the magnetic, or paramagnetic, field-sensed signal data and voltage gradient signal data are multidimensional data to which the exemplified processes facilitate the rebuilding of poor signals (and that can, among other benefits, tolerate heavy-tailed noise).

Van Der Pol Candidates in Sparse Approximation Operation

Referring still to FIG. 1, the sparse approximation operation 116, in some embodiments, includes searching Van der Pol candidates that are specified within the dictionary for a given nonlinearity parameter value and a given frequency parameter value that define each respective Van der Pol candidate. Each Van der Pol candidate, in some embodiments, is a pre-defined data set (e.g., a one-dimensional data set) that is generated from a solved Van der Pol-based differential equation as a steady-state solution defined by a nonlinearity value corresponding to a nonlinearity parameter μ and by a frequency value corresponding to a frequency parameter $\omega_i$.

Equation 1 shows an example modified Van der Pol differential equation that includes an embedded nonlinearity parameter μ and a frequency parameter $\omega_i$:

$$\ddot{x} - 2\mu\omega_i(1-x^2)\dot{x} + \omega_i^2 x = 0 \quad \text{(Equation 1)}$$

Each specified value of nonlinearity μ and frequency co, can be applied in Equation 1, and a solution can be obtained in the form of a data array having a pre-defined array length (e.g., t elements). For many value ranges of the nonlinearity parameter μ and the frequency parameter $\omega_i$, closed form solutions exist. For ranges of μ-parameter and $\omega_i$-parameter values not having a closed form solution, numerically stable methods, such as Runge-Kutta, may be used to numerically compute the solution. Other types of numerical methods for solving differential equations also may be used.

Equation 2 shows a state-space representation through which first-order approximation methods can be used to solve the modified Van der Pol equation of Equation 1 (where $x(t)=x_1(t)$):

$$\begin{cases} \dot{x}_1 = x_2 \\ \dot{x}_2 = 2\mu\omega_i(1-x_1)^2 - \omega_i^2 x_1 \end{cases} \quad \text{(Equation 2)}$$

FIG. 2 shows a diagram of a phase space representation of Van der Pol candidates as a Sine Homotopy Class $S_\mu(t, \omega_i)$ and as a Cosine Homotopy Class $C_\mu(t, \omega_i)$. The Sine-Homotopy-Class Van-der-Pol candidates and Cosine-Homotopy-Class Van-der-Pol candidates are shown for three different values of the nonlinearity parameter μ defining the Van der Pol candidate; namely, for μ=0.0 (202), for μ=0.5 (204), and for μ=1.0 (206), and where $\omega_i=2\pi$. As shown in FIG. 2, as the nonlinearity parameter μ increases, the non-linear dynamics of Equation 1 are observed or manifested as a homotopic deformation of a circle. To this end, decomposition of the information present in the first signal data set 102 and information in the second signal data set 104 into Van der Pol candidates can be performed for different values of the nonlinearity parameter μ, where the Van der Pol candidates for the varying nonlinearity parameter μ can be used to represent, or characterize, interesting linear and nonlinear information about the dynamics of the system. This can allow for a more accurate model-based representation of the signal of interest (e.g., data in the first signal data set 102 and in the second signal data set 104).

The Van der Pol candidates, in some embodiments, include a first candidate pool $C_\mu(t, \omega_i)$ defined as the Cosine Homotopy class (CHC) and a second candidate pool $S_\mu(t, \omega_i)$ defined as the Sine Homotopy class (SHC). The first candidate pool $C_\mu(t, \omega_i)$, in some embodiments, has a first set of initial conditions of $C_0(t, \omega_i)=\cos(\omega_i t)$ and second set of initial conditions of $x(0)=1$ and $\dot{x}(0)=0$. That is, for μ=0 (i.e., $C_0(t, \omega_i)$), the first candidate pool $C_\mu(t, \omega_i)$ is a cosine function of varying frequency values $\omega_i$. The second candidate pool $S_\mu(t, \omega_i)$, in some embodiments, has a first set of initial conditions of $S_0(t, \omega_i)=\sin(\omega_i t)$ and a second set of initial conditions of $x(0)=1$ and $\dot{x}(0)=\omega_i$. That is, for μ=0 (i.e., $S_0(t, \omega_i)$), the second candidate pool $S_\mu(t, \omega_i)$ is a sine function of varying frequency values $\omega_i$.

More specifically, when μ=0, the first candidate pool of the Cosine Homotopy Class is a cosine function and the second candidate pool of the Sine Homotopy Class is a sine function. In addition to the graphical solution shown in FIG. 2, this solution can be shown analytically. Notably, when μ=0, Equation 1 can be presented as Equation 3:

$$\ddot{x}+\omega_i^2 x=0 \quad \text{(Equation 3)}$$

Equation 3 has a general solution of $x(t)=a\cos(\omega_i t)+b\sin(\omega_i t)$, where the coefficients a and b depend on initial conditions as shown below in Equation 4.

$$x(0)=1 \text{ and } \dot{x}(0)=0 \rightarrow a=1 \text{ and } b=0 \rightarrow x(t)=\cos(\omega_i t)$$

$$x(0)=0 \text{ and } \dot{x}(0)=\omega_i \rightarrow a=0 \text{ and } b=1 \rightarrow x(t)=\sin(\omega_i t) \quad \text{(Equation 4)}$$

Examples of Van der Pol candidates for a Sine Homotopy Class and a Cosine Homotopy Class is now discussed. For example, for values of the nonlinearity parameter μ from 0 to 10, a first candidate pool of Van der Pol candidates based on the Sine Homotopy Class can be generated for some increment of μ; e.g., for each 0.1 increment of μ, or for each 0.01 increment of μ, or for each 0.001 increment of μ. Also, for the same values of the nonlinearity parameter μ from about 0 to about 10, a second candidate pool of Van der Pol candidates based on the Cosine Homotopy Class can be generated for some increment of μ; e.g., for each 0.1 increment of μ, or for each 0.01 increment of μ, or for each 0.001 increment of μ, etc. The size of the Van der Pol candidate pool (i.e., the dictionary) can thus vary, as indicated, based on the increment size.

The size of the Van der Pol candidate pool (i.e., the dictionary) can also vary based on the range of values of the frequency parameter $\omega_i$. For example, an embodiment of the dictionary can have a larger, and more granular, first candidate pool of Sine-Homotopy Class and a larger, and more granular, second candidate pool of Cosine Homotopy class for a frequency parameter $\omega_i$ from about 0 to about 100 (rather than from about 0 to about 10) in which a Van der Pol candidate is generated for some increment of $\omega_i$, e.g., for each 0.1 increment of $\omega_i$, for each 0.01 increment of $\omega_i$, or for each 0.001 increment of $\omega_i$. This list is not exhaustive, other ranges and increment values of μ and $\omega_i$ may be used in any combination.

In some embodiments, a range of the nonlinearity parameter μ is greater than 100. In other embodiments, a range of the nonlinearity parameter μ greater than 1000 is used. In yet other embodiments, a range of the frequency parameter $\omega_i$ greater than 100 is used. In some embodiments, a range of the frequency parameter $\omega_i$ greater than 1000 is used. In other embodiments, a range of the frequency parameter $\omega_i$ greater than 10,000 is used.

In some embodiments, the dictionary includes other candidate pools from other basis functions, including but not limited to wavelet packets, cosine packets, chirplets, complex exponential sinusoids, among others.

In some embodiments, upon selection of a candidate term for the first candidate pool $C_\mu(t, \omega_i)$ or the second candidate pool $S_\mu(t, \omega_i)$, a second selection is further made, within the same successive processing, corresponding to the other sine or cosine-based candidate pool. To this end, a selection of a value for the nonlinearity parameter μ and a selection of a value for the frequency parameter $\omega_i$ provides both $C_\mu(t, \omega_i)$ and $S_\mu(t, \omega_i)$ being added to the model for that value of the nonlinearity parameter μ and the frequency parameter $\omega_i$. We have found that for each sine or cosine candidate term (including the CHC and SHC terms) selected during a successive operation of a sparse approximation operation, the counterpart sine or cosine term is also subsequently selected. To this end, adding the counterpart sine or cosine term upon a determination of at least one of these terms reduces a likelihood of having to perform a successive operation to later identify that same counterpart sine or cosine term.

Each successive operation of the sparse approximation operation to determine the candidate terms involves the step of determining criteria for selecting the candidate term. These criteria may be based on determining a candidate term that produces a maximum reduction in mean square error in the signal of interest or a set of signals of interest. In some embodiments, a first candidate term is selected that produces the maximum reduction in mean square error, and a second candidate term is also selected in the same successive operation of a next relative maximum reduction in mean square error. Other types of criteria may be used, such as the weighted mean square error, maximum square error, among others. To this end, in some embodiments, four candidate terms are selected during each successive operation in the sparse approximation operation. Other numbers of candidate terms may be selected, such as six, eight, ten, etc. In some embodiments, the number of candidate terms selected per successive operation depends on the value of a successive operation that had previously been performed. For example, in some embodiments, the first 100 terms may be selected in 25 successive operations (in which four terms are concurrently selected) for each of the successive operations; and a fewer number of terms selected for each of the successive operations (e.g., one or two terms) after the first 100 terms have been selected.

Discussion of Van der Pol Candidates

Fourier analysis techniques can decompose a signal into different frequencies of sinusoidal functions. Sparse approximation techniques, such as matching pursuit, fast orthogonal searching, among others, can be used for spectral analysis methodologies according to which, e.g., a pair of sine and cosine functions are chosen in successive iterations. As provided herein, Van der Pol candidates include pairs of sine and cosine functions for the case the nonlinearity parameter μ=0.

In Fourier analysis, it can be assumed that y(t) is a periodic signal with a fundamental period of $T_0$ as shown in Equation 4

$$\text{(where } \omega 0 = \frac{2\pi}{T_0}; a_0 = \frac{1}{T_0}\int_{T_0} x(t)dt;$$

$$a_n = \frac{1}{T_0}\int_{T_0} x(t)\cos(n\omega_0 t)dt; \text{ and} \quad \text{(Equation 4)}$$

$$b_n = \frac{1}{T_0}\int_{T_0} x(t)\sin(n\omega_0 t)dt):$$

$$y(t) = a_0 + \sum_{n=1}^{\infty} a_n \cos(n\omega_0 t) + b_n \sin(n\omega_0 t)$$

Sinusoidal functions are a solution to differential equations, such as Equation 3. Indeed, $\cos(\omega t)$ and $\sin(\omega t)$ can be used to decompose a signal for different values of $\omega$. If one assumes that x(t) is not periodic, Fourier analysis reveals that a decomposition as shown in Equation 5 exists $$\text{(where } A(\omega) + \frac{1}{2\pi}\int_{-\infty}^{+\infty} x(t)\cos(\omega t)dt \text{ and} \quad \text{(Equation 5)}$$

$$B(\omega) = \frac{1}{2\pi}\int_{-\infty}^{+\infty} x(t)\sin(\omega t)dt):$$

$$y(t) + \int_{-\infty}^{+\infty} (A(\omega)\cos(\omega t) + B(\omega)\sin(\omega t))dw$$

To this end, the general solution of the differential equation of Equation 3 can be shown in Equation 6, where the coefficient a and b depend on initial conditions as shown in Equation 4.

$$x(t) = a \cdot \cos(\omega_i t) + b \cdot \sin(\omega_i t) \quad \text{(Equation 6)}$$

Simulation Results

We observed that Van der Pol candidate pools could be used to model a signal. FIGS. 4 and 5 show an example decomposition for a single lead cardiac biosignal using Van der Pol candidates, in accordance with an illustrative embodiment. Specifically, FIG. 4 shows a single lead cardiac biosignal 402 to be modeled, the signal having a sampling rate $f_s$ of about 1000 Hz and spanning about 10 seconds. FIG. 5 shows the same single lead biosignal 402 of FIG. 4 superimposed with three estimated signals 502, 504, and 506 generated using Van der Pol candidate pools, each having a non-linearity parameter $\mu$ value of 0.0, 0.5, and 1.0, respectively. The Van der Pol candidate pools, in this example, have a dense frequency spectral range spanning a minimum frequency (fMin) of 0.1 to a maximum frequency (fMax) of 3.0 in which the incremental step in frequency (df) is 0.01.

We have found that Van der Pol candidate pools can provide higher accuracy in modeling a signal than using only sine and cosine candidate pools. FIG. 6 shows a plot of model accuracies of Van der Pol candidate pools as a function of the number of terms used to represent the signal in accordance with an illustrative embodiment. Specifically, the y-axis of the plot shows the accuracy of the model as a fraction (e.g., 0.5 indicates the model being 50 percent accurate compared to the original signal; 1.0 indicates the model being 100 percent accurate compared to the original signal), etc.) and the x-axis shows the number of terms in a given model. As shown in FIG. 6, where $\mu$ is greater than zero (e.g., when $\mu$=0.5 (curve 602) and =1.0 (curve 604)), the estimated signals using Van der Pol candidates better represent the original signal (as compared to the signal generated using candidate pools associated with $\mu$=0.0 (curve 606)). As noted herein, when $\mu$=0.0, the Van der Pol candidate is a sine or cosine function.

As further shown in FIG. 6, for sine and cosine function-based candidates (e.g., curve 606), the model accuracy rises more quickly with each addition of the selected terms (as a function of the number of terms used to represent the signal) compared to Van der Pol candidates having a non-zero nonlinearity parameter value (e.g., curves 602 and 604), but is shown to saturate at around 98% accuracy (at about 300 terms) (point 610 on curve 606). Van der Pol candidates (e.g., as shown via curves 602 and 604) can achieve higher accuracies, approximating 100%, as the number of terms increases (see, e.g., accuracy levels of curves 602 and 604 in FIG. 6 for the number of model terms approaching 400 terms). The high model accuracies via the use of Van der Pol candidates, as demonstrated in the FIG. 6 illustration, facilitate de-noising of highly accurate magnetic, or paramagnetic, sensors (e.g., an optically pumped magnetometer), which in combination therewith has the potential of providing very sensitive and accurate measurements of biological or physiological signals and/or events related to a mammalian subject's heart, brain, etc. This ultimately allows for a more accurate understanding of the biological state of the subject whose signals are analyzed, leading to better and more accurate diagnoses and understanding of the presence and/or degree of any disease or conditions present with the subject that may require attention (including insight into any treatment such understanding may lead the subject's health care provider to prescribe).

Note that when measurements of the magnetic, or paramagnetic, sensors (or any sensors) are desired to provide very high accuracy of the data for analysis, modeling errors of, for example, 2 percent or more, can eliminate most, if not all, of the benefits of having very accurate and sensitive sensors. As such, modeling using Van der Pol candidate can ensure that modeling techniques employed on magnetic, or paramagnetic, sensors (or other types of highly sensitive and accurate sensors) do not mask the benefits of such sensors.

FIG. 7 shows a phase-space plot of an example decomposition for a three-lead cardiac biosignal, in accordance with an illustrative embodiment. The plot includes a three-lead cardiac biosignal 702 (in which each lead corresponds to one of the axes x(t), y(t), and z(t)), and a corresponding estimated/modeled signal 704 is generated using candidate pools having a non-linear parameter $\mu$ of 1.0. As illustrated by the qualitative similarities of curves 702 and 704 in FIG. 7's phase-space plot, Van der Pol candidate pools provide an estimated or modeled signal that fairly well tracks the original signal. In FIG. 7, each of the axes is scaled to a normalized measure of the amplitude of a given signal used for the respective axes. It may be voltages (e.g., milli-volts), current (e.g., milli-amperes), magnetic field (e.g., nanotesla), depending on the sensor.

Method of Operation

FIG. 8 is a diagram illustrating a process to de-noise a first signal data set (e.g., element 102 in FIG. 1) by generating a sparse approximation of the data therein in conjunction with data present in a second signal data set (e.g., element 104 in FIG. 1), in accordance with an illustrative embodiment. As discussed herein, the approximated first signal data set (e.g., element 102) is used in the analysis (e.g., element 118 of FIG. 1) to non-invasively identify and/or measure or estimate a degree of myocardial ischemia, identifying one or more stenoses, and/or localizing and/or estimating fractional flow reserve (e.g., element 122 of FIG. 1) of a mammalian subject such as a human.

As shown in FIG. 8, the illustrated method 800 includes at step 802 receiving, by one or more processors, a first signal data set (e.g., 102), comprising data such as of, e.g., magnetic-, or paramagnetic-, field-sensed signal, acquired or captured from a first set of sensor leads (e.g., 108a, 108b, etc.) associated with a first sensor type (e.g., magnetometer), and a second signal data set (e.g., 104) comprising data such as of voltage-, current-, or impedance-, field-sensed signals acquired or captured from a second set of sensor leads, associated with a second sensor type, for example, biopotential surface probes. Information in magnetic-, or paramagnetic-, field-sensed signals are simultaneously sampled or captured with voltage-, current-, or impedance-, field-sensed signals. As such, a given biological, particularly electrophysiological or magneto-physiological events, captured within the first signal data set (e.g., 102) will have a corresponding presence in the second signal data set (e.g., 104).

In some embodiments, the magnetic-, or paramagnetic-, field-sensed signal data are acquired from one or more zero-field optically pumped magnetometer sensors.

In some embodiments, the biopotential surface probe data associated with the mammalian subject are acquired from a single biopotential probe. In other embodiments, the biopotential surface probe data are acquired from multiple biopotential probe sets, such as a 3-lead orthogonal set or a 12-lead set.

Other types of sensor leads may be used, including electrical current probes, optical probes, impedance probes, and acoustic probes, among others.

Referring still to FIG. 8, the method 800 includes at step 804 determining, by the one or more processors, one or more candidate basis functions searched through, and selected from, a dictionary of candidate basis functions, wherein the plurality of candidate basis functions are aggregable (e.g., as a linear combination of a weighted sum) to represent the sparse approximation of the first signal data set and the second signal data set. In some embodiments, the candidate basis functions include but are not limited to Van der Pol candidates, wavelet packets, cosine packets, chirplets, and/or complex exponential sinusoids.

The method 800 further includes at step 806 determining, via the one or more processors, one or more coronary physiological parameters of the subject selected from the group consisting of a fractional flow reserve estimation, a stenosis value, and a myocardial ischemia estimation, based in part on low-energy subspace components of the sparse approximation of the first signal data.

Fractional flow reserve is generally a measure of blood pressure and flows through a specific part of a subject's coronary artery. The exemplified methods and systems facilitate the estimation of fractional flow reserve using non-invasive operations that do not use or require direct physical measurements of flow and pressure characteristics in a given coronary artery.

Myocardial ischemia is a condition of inadequate blood supply, and thus oxygen supply, to heart tissue.

Stenosis is an abnormal narrowing of a body channel, such as of the coronary vessels and capillaries.

The low-energy subspace components comprise a model reconstructed by using only the X % low magnitude subset coefficients (frequency content) contributing least to the modelling error. Low-energy subspace components, in some embodiments, includes higher-order candidate terms that are later selected, in the phase space coordinates, as part of the sparse representation of a signal. That is, the last 5 percent, 10 percent, 15 percent, 20 percent, 25 percent, 30 percent of the candidate terms (as the higher-order candidate terms) last selected via the sparse approximation is used. Other percentage values can be used.

Optically Pumped Magnetometer

Referring to the embodiment of FIG. 1, system 100 can include one or more magnetic, or paramagnetic, sensors 108 (shown as 108a and 108b) (each, e.g., an optically pumped magnetometer). An optically pumped magnetometer typically comprises a laser 124 and a photodetector 126 to detect changes in the resonance of a "sensing" gas 128, enclosed in a vapor cell 130, that is sensitive to minute changes in weak magnetic fields.

Examples of optically pumped magnetometers that detect zero-field resonance are described in U.S. Publication No. 2015/0212168 and U.S. Publication No. 2016/0223627, each of which is incorporated by reference herein in its entirety.

An optically pumped magnetometer, in some embodiments, relies on detecting changes in the optical transmission properties of atomic vapor (e.g., an alkali metal vapor) around a narrow, zero-field atomic resonance to measure the magnitude and direction of the background magnetic field. In some embodiments, the zero-field resonance is observed when the atomic vapor in the optically pumped magnetometer is subjected to very small magnetic fields, generally less than 100 nT. In some embodiments, the full width of the zero-field resonance is less than 30 nT.

Other types of magnetic-, or paramagnetic-based sensors and other types of sensors may be used with the technique described herein. FIG. 3 shows a diagram of magnetic-field ranges typically used for magneto-cardiography and magneto-encephalography.

Biopotential-Based Measurement Equipment and Sensors

Referring to the embodiment of FIG. 1, system 100 includes biopotential-based measurement equipment 112, which, in some embodiments, is wide-band biopotential measuring equipment that, in the cardiography context, captures cardiac-related biopotential or electrophysiological signals of a mammalian subject such as a human as wide-band cardiac phase gradient signals. Such equipment 112 may capture other mammalian biopotential or electrophysiological signals, such as, e.g., cerebral biopotential signals.

As described in U.S. Publication No. 2017/0119272 and in U.S. patent application Ser. No. 15/248,838, each of which is incorporated by reference herein in its entirety, the biopotential-based measurement equipment 112, in some embodiments, is configured to capture unfiltered mammalian electrophysiological signals such that the spectral component(s) of the signals are not altered. That is, all of the captured signal, if not a significant portion of the captured signal, includes, and does not exclude, components conventionally perceived/treated as and filtered out as noise (e.g., including those in the frequency range of greater than about 1 kHz). Further, the biopotential-based measurement equipment 112 of FIG. 1 can capture, convert, and even analyze the collected wide-band biopotential signals without any filtering (via, e.g., hardware circuitry and/or digital signal processing techniques, etc.) that otherwise can affect the phase linearity of the signal of interest in the wide-band biopotential signals.

In some embodiments, the biopotential-based measurement equipment 112 include wide-band equipment configured to capture one or more biosignals of a subject, such as mammalian biopotential signals, in microvolt or sub-microvolt resolutions—resolutions that are at, or significantly below, the noise floor of conventional electrocardiographic and other biosignal acquisition instruments. In some embodiments, the wide-band biopotential measuring equipment is configured to acquire and record wide-band phase gradient signals (e.g., wide-band cardiac phase gradient signals, wide-band cerebral phase gradient signals) that are simultaneously sampled, in some embodiments, having a temporal skew or "lag" of less than about 1 µs, and in other embodiments, having a temporal skew or lag of not more than about 10 femtoseconds. Notably, the exemplified system minimizes non-linear distortions (e.g., those that can be introduced via certain filters) in the acquired wide-band phase gradient signal so as to not affect the information therein.

Phase Space Transformation and Analysis

As described in U.S. patent application Ser. No. 15/248,838, a phase space analysis system is configured to generate a phase space map to be used in subsequent phase space analysis. The output of the phase space analysis is then evaluated using machine learning analysis to assess parameters associated with a presence and/or degree of a disease or physiological characteristic (such as, e.g., in the cardiovascular context, regional arterial flow characteristics). In some embodiments, the machine learning analysis may use a library of quantified FFR, stenosis, and ischemia data (e.g., data acquired from a study of coronary arterial disease) in the assessment of the obtained wide-band cardiac gradient signal data.

The output of a processor performing the analysis may then be transmitted to a graphical user interface, such as, e.g., a touchscreen or other monitor, for visualization. The graphical user interface, in some embodiments, is included in a display unit configured to display values of any number of parameters discussed herein and elsewhere. In some embodiments, the graphical user interface displays these data in formats such as, e.g., a three-dimensional phase space plot representation of the biopotential signal data and virtual biopotential signal data. In other embodiments, the data output of the processor is or may also be simultaneously or sequentially transmitted to one or more non-graphical user interfaces (e.g., printout, command-line or text-only user interface), directly to a database or memory device, processor, firmware, hardware and/or software for, e.g., later retrieval and/or additional analysis, other machines that may include non-graphical user interfaces for the display of such data, or combinations thereof. Any device, machine, or medium capable of receiving data and being interpreted by a human or machine or used for further processing is contemplated and within the scope of the present disclosure.

FIG. 9 is a diagram of an exemplary method 900 of processing the fused signal data set 120 in accordance with an illustrative embodiment. The method 900 includes collecting and fusing data in the first signal data set 102 and data in the second signal data set 104 to form the fused signal data set 120 and then pre-processing 902 this data set 120 to generate, via phase space analysis techniques, a phase space data set (shown as "residue subspace" data set 904 and "noise subspace" data set 906). The characteristics of the phase space data set (904, 906) and fused input data set (916) may be extracted in a feature extraction operation (e.g., analysis steps 918, 922, 926), to determine geometric and dynamic properties of the data set. These subspaces may include but are not limited to complex subharmonic frequency (CSF) trajectory, quasi-periodic and chaotic subspaces, low/high energy subspaces, and fractional derivatives of the low/high energy subspaces. These subspaces are exemplars of the family of subspaces that characterize the dynamics of the system, whether pathological or normal.

The extracted metrics (912a, 912b, 912b) can be evaluated via, e.g., nested non-linear functions 910 (associated with stenosis and/or FFR models) to estimate values 122 for a given subject related to, e.g., regional FFR, the presence and/or degree of stenosis, ischemia, etc. In some embodiments, the values associated with regional FFR and the presence and/or degree of the stenosis and ischemia are then mapped to a point-cloud representation of a three-dimensional model of the heart.

Analysis using phase space analysis techniques as described herein can facilitate understanding of different bioelectric structures within mammalian tissue, including but not limited to tissue in or associated with organs such as the brain or the heart. For example, various types of cardiac tissue, particularly but not necessarily when such tissue is/are damaged or unhealthy, may exhibit different conduction characteristics, such as can be exhibited by differences in tissue impedance. Indeed, these techniques can be used to understand spectral, and non-spectral conduction delays and bend in the trajectory of the phase space orbit as it propagates through the heart. These small changes in trajectory can further be normalized and quantified on a beat-to-beat basis and corrected for abnormal or poor lead placement. The normalized phase space integrals can also be visualized on, or mapped to, a geometric mesh (e.g., a model of the heart) using a genetic algorithm. In some embodiments, these phase space integrals are mapped to myocardial segments in the heart. In some embodiments, these mapped myocardial segments can correspond to the 17-segments of the left ventricular model of the heart. Other numbers of myocardial segments may be used.

In some embodiments, the phase space integrals can be spatially mapped to a generic/standard or a customized model of hearts, for example, derived from various tomographic imaging modalities, such as CT (computed tomography), MRI (magnetic resonance imaging), PET (positron emission tomography), and etc.

Referring still to FIG. 9, three distinct phase space analyses are performed to generate sets of metrics and variables (shown as steps 912a, 912b, and 912c). The metrics and variables are then used in the non-linear functions (e.g., as shown in step 910) to generate regional FFR estimation values, regional stenosis values, and regional ischemia values 122. Table 1 is an example output matrix of these values 122.

TABLE 1

| Segment | Vessel | FFR | Stenosis | Ischemia |
| --- | --- | --- | --- | --- |
| 1 | Left Main Artery (LMA) | 0.90 | 0.50 | 0.20 |
| 2 | Proximal Left Circumflex Artery (Prox LCX) | 0.85 | 0.60 | 0.30 |
| 3 | Mid- Left Circumflex Artery (Mid LCX) | 0.93 | 0.35 | 0.15 |
| 4 | Distal Left Circumflex Artery (Dist LCX) | 1.00 | 0.00 | 0.00 |
| 5 | Left Posterior Atrioventricular (LPAV) | 1.00 | 0.00 | 0.00 |
| 6 | First Obtuse Marginal (OM1) | 0.60 | 0.95 | 0.72 |
| 7 | Second Obtuse Marginal (OM2) | 1.00 | 0.00 | 0.00 |
| 8 | Third Obtuse Marginal (OM3) | 1.00 | 0.00 | 0.00 |
| 9 | Proximal Left Anterior Descending Artery (Prox LAD) | 1.00 | 0.00 | 0.00 |
| 10 | Mid Left Anterior Descending Artery (Mid LAD) | 1.00 | 0.00 | 0.00 |
| 11 | Distal Left Anterior Descending Artery (Dist LAD) | 0.70 | 0.80 | 0.63 |

TABLE 1-continued

| Segment | Vessel | FFR | Stenosis | Ischemia |
|---|---|---|---|---|
| 12 | LAD D1 | 0.00 | 0.00 | 0.75 |
| 13 | LAD D2 | 0.00 | 0.00 | 0.00 |
| 14 | Proximal Right Coronary Artery (Prox RCA) | 0.00 | 0.00 | 0.00 |
| 15 | Mid Right Coronary Artery (Mid RCA) | 0.00 | 0.00 | 0.00 |
| 16 | Distal Right Coronary Artery (Dist RCA) | 0.00 | 0.00 | 0.18 |
| 17 | Acute Marginal Brach Right of the Posterior Descending Artery (AcM R PDA) | 0.00 | 0.00 | 0.00 |

As shown, Table 1 includes numerical values for a fractional flow reserve (FFR) parameter, an estimated stenosis parameter, and an estimated ischemia parameter for a plurality of (in this case, 17) segments corresponding to major vessels of a human heart. In some embodiments, matrix of the value 122 includes numerical values of a fractional flow reserve (FFR) parameter, an estimated stenosis parameter, and an estimated ischemia parameter for a standardized myocardial segment map having 17 segments of the heart including the Left Main Artery (LMA), the Proximal Left Circumflex Artery (Prox LCX), the Mid-Left Circumflex Artery (Mid LCX), the Distal Left Circumflex Artery (Dist LCX), the Left Posterior Atrioventricular (LPAV), the First Obtuse Marginal Branch (OM1), the Second Obtuse Marginal Brach (OM2), the Third Obtuse Marginal Branch (OM3), the Proximal Left Anterior Descending Artery (Prox LAD), the Mid Left Anterior Descending Artery (Mid LAD), the Distal Left Anterior Descending Artery (Dist LAD), the Left Anterior Descending First Diagonal Branch (LAD D1), the Left Anterior Descending Second Diagonal Branch (LAD D2), the Proximal Right Coronary Artery (Prox RCA), the Mid Right Coronary Artery (Mid RCA), the Distal Right Coronary Artery (Dist RCA), and the Acute Marginal Brach Right of the Posterior Descending Artery (AcM R PDA).

In Table 1, the parameter values for myocardial ischemia estimation, stenosis identification, and/or fractional flow reserve estimation are shown in a range of 0 to 1. Other scaling or ranges may be used, such as other non-numerical values, to indicate a relative degree of the parameter of interest compared to a nominal standard.

Tables 2-5 show example non-linear functions used to generate FFR estimations for several segments corresponding to major vessels in the heart. In Table 2, an example function to determine an FFR estimation for the left main artery ("FFR_LEFTMAIN") is provided.

TABLE 2

FFR_LEFTMAIN =
0.128467341682411*noisevectorRz*atan2(Alpharatio, DensityV4)

As shown in Table 2, the FFR estimation for the left main artery is determined based on extracted metrics and/or variables such as a Z-component parameter associated with the noise subspace ("noisevectorRz"), an Alphahull ratio parameter ("Alpharatio"), and a signal density cloud volume 4 ("DensityV4").

In Table 3, an example function to determine an FFR estimation for the mid right coronary artery ("FFR_MIDRCA") is provided.

TABLE 3

FFR_MIDRCA =
0.0212870065789474*noisevectorRy*Alpharatio*DensityV3

As shown in Table 3, the FFR estimation for the mid right coronary artery is determined based on extracted metrics and/or variables such as a Y-component parameter associated with the noise subspace ("noisevectorRy"), the Alphahull ratio parameter ("Alpharatio"), and a signal density cloud volume 3 ("DensityV3").

In Table 4, an example function to determine an FFR estimation for the mid left artery descending ("FFR_MIDLAD") is provided.

TABLE 4

FFR_MIDLAD = atan2(AspectRatio3, residueLevelMean)

As shown in Table 4, the FFR estimation for the mid left artery descending is determined based on extracted metrics and/or variables such as a ratio of volume to surface area for cloud cluster 3 ("AspectRatio3") and a wavelet residue mean XYZ ("residueLevelMean").

In Table 5, an example function to determine an FFR estimation for the proximal left circumflex artery ("FFR_PROXLCX") is provided.

TABLE 5

FFR_PROXLCX =
0.408884581034257*atan2(residueLevelVolume + vectorcloud6, DensityV4)

As shown in Table 5, the FFR estimation for the proximal left circumflex artery is determined based on extracted metrics and/or variables such as a wavelet residue volume XYZ ("residueLevelVolume"), vector cloud 6 volume ("vectorcloud6"), and a signal density cloud volume 4 ("DensityV4").

FIG. 10 is a diagram of a method of performing machine learning analysis to create and select non-linear models to identify and/or estimate a degree of myocardial ischemia, identify and/or estimate a degree of one or more stenoses, and/or localize and/or estimate fractional flow reserve, in accordance with an illustrative embodiment. As shown in FIG. 10, angiographic data set 1002, and fractional flow data set 1004 are used to create (via operation 1006) candidate non-linear models to identify one or more stenoses (and/or estimate a degree thereof) and estimate fractional flow reserve (FFR) 1014. Examples of the generation of non-linear models to estimate, e.g., cardiac chamber size and mechanical function, are described in U.S. application Ser. No. 14/295,615, titled "Noninvasive electrocardiographic method for estimating mammalian cardiac chamber size and mechanical function," which is incorporated by reference herein in its entirety.

In some embodiments, machine learning algorithms 1008 are then used to select a family of non-linear models 1010 from the candidate non-linear models using wide-band gradient cardiac signal data 1012 of patients or subjects with some degree of stenosis and ischemia. In some embodiments, the machine learning algorithms are based on Regression Random forest algorithms or a variation thereof. In some embodiments, the machine learning algorithms are based on deep learning algorithms.

In some embodiments, the machine learning stage invokes a meta-genetic algorithm to automatically select a subset of features drawn from a large pool. This feature subset is then used by an Adaptive Boosting (AdaBoost) algorithm to generate predictors to diagnose significant coronary artery disease across a population of patients representing both positive and negative cases. The performances of the candidate predictors are determined through verification against a previously unseen pool of patients. A further description of the AdaBoost algorithm is provided in Freund, Yoav, and Robert E. Schapire, "A decision-theoretic generalization of on-line learning and an application to boosting," European conference on computational learning theory. Springer, Berlin, Heidelberg (1995), which is incorporated by reference herein in its entirety.

To determine the presence or degree of ischemia, in some embodiments, spatial changes in the phase space matrix can be extracted using a non-Fourier integral, which creates 12-dimensional space-time density metrics. These metrics for the ventricle are modeled using a genetic algorithm to link 17 nonlinear nested sinusoidal Gaussian equations, for the 17 segments of the coronary arterial territories, as perfusion blockages. Perfusion images can be visually scored using a 17-segment model of the heart by a 5-point scale (0=normal tracer uptake, 1=mildly reduced, 2=moderately reduced, 3=severely reduced, 4=no uptake). The amount of ischemic myocardial tissue (IM) can be calculated based on a summed difference of the score (the difference between summed stress and summed rest scores). Patients can then be classified as: no ischemia or equivocal (IM<5%), mild ischemia (5%≤IM<10%), and moderate/severe ischemia (IM≥10%). The output of these equations provides the amount and location of the ischemic myocardial tissue.

FIG. 11 is a diagram of a method of visualizing the estimated arterial flow characteristics in the heart, in accordance with an illustrative embodiment. As shown in FIG. 11, a visualization engine 1102 receives the determined arterial flow characteristics (such as FFR or stenosis values 122) and renders the characteristics onto a three-dimensional visualization output. In some embodiments, the visualization engine 1102 provides, in a graphical user interface (GUI), a system-level view of all of the arterial flow characteristics and their interactions. In some embodiments, the GUI presents the cascading effects of upstream modifications to the arterial flow upon the downstream circulation.

Further examples of phase space processing that may be used with the exemplified method and system are described in U.S. Provisional Patent Application No. 62/184,796, title "Latent teratogen-induced heart deficits are unmasked postnatally with mathematical analysis and machine learning on ECG signals"; U.S. patent application Ser. No. 15/192,639, title "Methods and Systems Using Mathematical Analysis and Machine Learning to Diagnose Disease"; U.S. patent application Ser. No. 14/620,388, published as US2015/0216426, title "Method and System for Characterizing Cardiovascular Systems From Single Channel Data"; U.S. patent application Ser. No. 14/596,541, issued as U.S. Pat. No. 9,597,021, title "Noninvasive Method for Estimating Glucose, Glycosylated Hemoglobin and Other Blood Constituents"; U.S. patent application Ser. No. 14/077,993, published as US2015/0133803, title "Noninvasive Electrocardiographic Method for Estimating Mammalian Cardiac Chamber Size and Mechanical Function"; U.S. patent application Ser. No. 14/295,615, title "Noninvasive Electrocardiographic Method for Estimating Mammalian Cardiac Chamber Size and Mechanical Function"; U.S. patent application Ser. No. 13/970,582, issued as U.S. Pat. No. 9,408,543, title "Non-invasive Method and System for Characterizing Cardiovascular Systems and All-Cause Mortality and Sudden Cardiac Death Risk"; U.S. patent application Ser. No. 15/061,090, published as US2016/0183822, title "Non-invasive Method and System for Characterizing Cardiovascular Systems"; U.S. patent application Ser. No. 13/970,580, issued as U.S. Pat. No. 9,289,150, title "Non-invasive Method and System for Characterizing Cardiovascular Systems"; U.S. Patent Application No. 62/354,668, titled "Method and System for Phase Space Analysis to Determine Arterial Flow Characteristics"; and U.S. Provisional Patent Application No. 61/684,217, title "Non-invasive method and system for Characterizing Cardiovascular System, " which are each incorporated by reference in its entirety.

While the methods and systems have been described in connection with certain embodiments and specific examples, it is not intended that the scope be limited to the particular embodiments set forth, as the embodiments herein are intended in all respects to be illustrative rather than restrictive.

For example, in addition to fusing and de-noising data from heterogeneous sensor types, the methods, processes, and systems described herein can be used to de-noise signals captured from a subset of leads of a larger set (e.g., a homogenous sensor types), for example, where noise issues have been observed in a subset of leads.

Although the disclosure refers to magnetic, or paramagnetic, field-sensed signal data, the methods, processes, and systems described herein can be used to de-noise other types of signal data (e.g., electrophysical signal data) by fusing a first noisy signal data set with a second signal data set simultaneously captured from a same source. In particular, it is contemplated that different electrophysiological phenomena originating from the same source can be de-noised (i.e., cleaned). Examples of such electrophysiological phenomena that can be measured and used with the exemplary methods, processes, and systems described herein include blood pressure variations, pulse oximetry information, cardiac magnetic field information, cardiac ballistics, and various traditional electrophysical measurements. The data sets associated with these electrophysiological phenomena can be used with magnetic, or paramagnetic, field-sensed signal data set and/or voltage gradient signal data set discussed herein.

The methods, systems and processes described herein may be used to generate stenosis and FFR outputs for use in connection with procedures such as the placement of vascular stents within a vessel such as an artery of a mammalian (e.g., human) subject and other interventional and surgical system or processes. In one embodiment, the methods, systems, and processes described herein can be configured to use the FFR/stenosis outputs to determine and/or modify, intra operation, a number of stents to be placed in a mammalian (e.g., human), including their optimal location of deployment within a given vessel, among others.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow;

plain meaning derived from grammatical organization or punctuation; the number or type of embodiments described in the specification.

In some embodiments, the signal reconstruction process can be a universal signal decomposition and estimation processing method that is agnostic to a type of sensor/data.

What is claimed is:

1. A method to de-noise data associated with a first set of biosignals by generating a sparse approximation of a first biosignal data set in conjunction with data associated with a second set of biosignals, wherein the approximated first biosignal data set is used in an analysis to non-invasively identify and/or measure or estimate a degree of a clinical pathology, the method comprising:

receiving, by one or more processors, i) the first biosignal data set associated with one or more first biosignals acquired from a first set of sensor leads associated with a first sensor type and ii) a second biosignal data set associated with one or more second biosignals captured from a second set of sensor leads, associated with a second sensor type, wherein the first sensor type is different from the second sensor type, and wherein the one or more first biosignals are simultaneously captured with the one or more second biosignals;

determining, by the one or more processors, one or more candidate basis functions searched through, and selected from, a dictionary of candidate basis functions, wherein the plurality of candidate functions is aggregable to represent the sparse approximation of the first biosignal data and the second biosignal data; and determining, via the one or more processors, one or more physiological parameters of the subject.

2. The method of claim 1, wherein the dictionary of candidate basis functions comprises a set of candidate basis functions derived from one or more homotopic non-linear differential equations, the homotopic non-linear differential equations having a homotopy class, wherein each candidate basis function of the set of candidate basis functions is a solution of a given homotopic non-linear differential equation having a specific first embedding parameter value from a set of first embedding parameter values and a specific second embedding parameter value from a set of second embedding parameter values.

3. The method of claim 2, wherein the one or more homotopic non-linear differential equation are based on a Van der Pol differential equation.

4. The method of claim 2, wherein the one or more homotopic non-linear differential equations are selected from the group consisting of Lorenz-based equations, Rössler-based equations, and a Van der Pol-based equation.

5. The method of claim 2, wherein the sparse approximation operation of determining the plurality of candidate basis functions is performed according to cyclical coordinate descent using a set of Van der Pol candidates, wherein each set of the Van der Pol candidates is defined by a nonlinearity parameter value and a frequency parameter value.

6. The method of claim 2, wherein the operation of determining the plurality of candidate basis functions is performed according to an algorithm selected from the group consisting of modified matching pursuit, evolvable mathematical models, symbolic regression, orthogonal matching pursuit, least absolute shrinkage and selection operator (LASSO), linear models optimized using cyclical coordinate descent, orthogonal search, fast orthogonal search, and any variations or combinations of any of the above.

7. The method of claim 1, wherein the sparse approximation of the first biosignal data set is a linear combination of weighted sums of a plurality of selected candidate basis function, and wherein low-energy subspace components of the sparse approximation of the first biosignal data set are determined as a subset of said weighted sums.

8. The method of claim 7, wherein the low-energy subspace components comprise a last set percentile of the plurality of selected candidate basis functions, wherein the percentile is selected from the group consisting of about a last 10 percent, about a last 15 percent, about a last 20 percent, and about a last 25 percent.

9. The method of claim 1, wherein the sparse approximation of the first biosignal data comprises a linear combination of over 100 selected candidate basis function, and wherein at least two candidate basis functions are selected at one or more successive stages when determining the one or more candidate basis functions searched from the dictionary of candidate basis functions.

10. The method of claim 9, wherein the at least two selected candidate basis functions selected at each successive stage include i) a first candidate basis function derived from one or more homotopic non-linear differential equations having a homotopy class and ii) a second candidate basis function derived from the one or more homotopic non-linear differential equations having a homotopy class, and wherein the first candidate basis function is about 90 degree phase offset from the second candidate basis function.

11. The method of claim 9, wherein at least four candidate basis functions are selected at one or more successive stages when searched across the dictionary of candidate basis functions, the method comprising:

determining, by the one or more processors, a plurality of values associated with a measure of reduction of error of approximating the first biosignal data set, wherein a first set of at least two candidate basis functions are selected based for a highest values of the plurality of values associated with the measure of reduction of error and wherein a second set of two candidate basis functions are selected based for a next highest of the plurality of values associated with the measure of reduction of error determined at a same successive stage.

12. The method of claim 11, wherein the first set of at least two candidate basis functions includes a first candidate basis function derived from one or more homotopic non-linear differential equation having homotopic class and a second candidate basis function derived from the one or more homotopic non-linear differential equation having homotopic class, wherein the first candidate basis function has about 90-degree phase offset from the second candidate basis function.

13. The method of claim 7, wherein the at least one of the candidate basis functions comprises a Van der Pol-based differential equation with a forcing function.

14. The method of claim 13, wherein the Van Der Pol-based differential equation with the forcing function is expressed as:

$$\ddot{x} - 2\mu\omega_i(1-x^2)\dot{x} + \omega_i^2 x = 0$$

wherein $\mu$ is an embedding parameter corresponding to a measure of nonlinearity.

15. The method of claim 1, wherein the first biosignal data set comprises magnetic-, or paramagnetic-, field-sensed biosignal data.

16. The method of claim 1, wherein the first biosignal data set is captured from a surface-based vector magnetometer configured to operate at room temperature.

17. The method of claim 1, wherein the first biosignal data set is captured from a surface-based vector magnetometer configured to operate within ambient magnetic field below 30 nT (nanotesla).

18. The method of claim 1, wherein the second biosignal data set comprises wide-band cardiac phase gradient biosignal data or wide-band cerebral phase gradient biosignal data derived from biopotential biosignals simultaneously captured from a plurality of surface electrode placed on the subject.

19. The method of claim 1, wherein the first biosignal data set is acquired from a different sensor type from that of the second biosignal data set, and wherein the second biosignal data set is captured by a sensor system selected from the group consisting of a magnetic-resonance imaging (MRI) system, a computed tomography (CT) system, a positron emission tomography (PET) system, a ultrasound system, and an electrical impedance system.

* * * * *